(12) United States Patent
Ogawa et al.

(10) Patent No.: US 10,468,608 B2
(45) Date of Patent: Nov. 5, 2019

(54) ORGANIC-ELECTROLUMINESCENT-ELEMENT MATERIAL, AND ORGANIC ELECTROLUMINESCENT ELEMENT USING SAME

(71) Applicant: NIPPON STEEL & SUMIKIN CHEMICAL CO., LTD., Tokyo (JP)

(72) Inventors: Junya Ogawa, Kitakyushu (JP); Tokiko Ueda, Kitakyushu (JP); Masashi Tada, Kitakyushu (JP); Takahiro Kai, Kitakyushu (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 0 days.

(21) Appl. No.: 15/560,796

(22) PCT Filed: Mar. 17, 2016

(86) PCT No.: PCT/JP2016/058506
§ 371 (c)(1),
(2) Date: Sep. 22, 2017

(87) PCT Pub. No.: WO2016/158454
PCT Pub. Date: Oct. 6, 2016

(65) Prior Publication Data
US 2018/0114908 A1    Apr. 26, 2018

(30) Foreign Application Priority Data
Mar. 30, 2015    (JP) .................................. 2015-070114

(51) Int. Cl.
*H01L 51/00*    (2006.01)
*C09K 11/06*    (2006.01)
(Continued)

(52) U.S. Cl.
CPC .............. *H01L 51/008* (2013.01); *C07F 5/027* (2013.01); *C09K 11/06* (2013.01); *H01L 51/50* (2013.01);
(Continued)

(58) Field of Classification Search
CPC ............... H01L 51/008; H01L 51/0085; H01L 51/0058; H01L 51/0072; H01L 51/0073;
(Continued)

(56) References Cited

U.S. PATENT DOCUMENTS

2002/0034655 A1    3/2002   Watanabe et al.
2012/0319088 A1    12/2012  Lee et al.

FOREIGN PATENT DOCUMENTS

JP    2005-162709 A    6/2005
JP    2005-166574 A    6/2005
(Continued)

OTHER PUBLICATIONS

English Translation of International Preliminary Report on Patentability (PCT/IPEA/409) for Application No. PCT/JP2016/058506 dated Oct. 5, 2017.
(Continued)

*Primary Examiner* — Eli D. Strah
(74) *Attorney, Agent, or Firm* — Cheng Law Group, PLLC

(57) ABSTRACT

Provided are an organic EL device having high efficiency and high driving stability, and a compound suitable for the device. Provided is a material for an organic electroluminescent device formed of a carborane compound having a structure in which: one or two boron atoms of a carborane ring $C_2B_{10}H_{12}$ are substituted with an aromatic hydrocarbon group or an aromatic heterocyclic group; and the two carbon atoms of the carborane ring are each bonded to an aromatic hydrocarbon group or an aromatic heterocyclic group, or are
(Continued)

each bonded to any other carborane ring when a plurality of carborane rings are present. Also provided is an organic electroluminescent device in which the material for an organic electroluminescent device is used in a light-emitting layer, an electron-transporting layer, or a hole-blocking layer.

10 Claims, 1 Drawing Sheet

(51) Int. Cl.
  *H01L 51/50* (2006.01)
  *C07F 5/02* (2006.01)
  *C07D 209/86* (2006.01)
  *C07D 307/91* (2006.01)
  *C07D 405/10* (2006.01)
  *C07D 405/14* (2006.01)
  *C09K 11/02* (2006.01)
  *H05B 33/20* (2006.01)

(52) U.S. Cl.
  CPC ...... *B32B 2457/206* (2013.01); *C07D 209/86* (2013.01); *C07D 307/91* (2013.01); *C07D 405/10* (2013.01); *C07D 405/14* (2013.01); *C07F 5/02* (2013.01); *C09K 11/025* (2013.01); *C09K 2211/1007* (2013.01); *C09K 2211/1011* (2013.01); *C09K 2211/1022* (2013.01); *C09K 2211/1029* (2013.01); *C09K 2211/1088* (2013.01); *H01L 51/0058* (2013.01); *H01L 51/0072* (2013.01); *H01L 51/0073* (2013.01); *H01L 51/0085* (2013.01); *H01L 51/5016* (2013.01); *H01L 51/5072* (2013.01); *H01L 51/5096* (2013.01); *H05B 33/20* (2013.01)

(58) Field of Classification Search
  CPC ............. H01L 51/5016; H01L 51/5072; H01L 51/5096; H01L 51/50; C07F 5/027; C07F 5/02; C09K 11/06; C09K 11/025; C09K 2211/1011; C09K 2211/1029; C09K 2211/1007; C09K 2211/1088; C09K 2211/1022; C07D 405/10; C07D 405/14; C07D 307/91; C07D 209/86; B32B 2457/206; H05B 33/20
  See application file for complete search history.

(56) References Cited

FOREIGN PATENT DOCUMENTS

| JP | 2016-9824 A | 1/2016 |
| WO | WO-2013/094834 A1 | 6/2013 |
| WO | WO-2014/103724 A1 | 7/2014 |
| WO | WO-2014/103910 A1 | 7/2014 |
| WO | WO-2014103724 A1 * | 7/2014 ......... H01L 51/0058 |

OTHER PUBLICATIONS

International Search Report for the Application No. PCP/JP2016/058506 dated May 31, 2016.
Wee, Kyung-Ryang et al., "Carborane-Based Optoelectronically Active Organic Molecules: Wide Band Gap Host Materials for Blue Phosphorescence", Journal of the American Chemical Society, 2012, vol. 134, pp. 17982-17990.
Dash, Barada Prasana et al., "Synthesis and Properties of Carborane-Appended $C_3$-Symmetrical Extended π Systems", Journal of the American Chemical Society, 2010, vol. 132, pp. 6578-6587.

* cited by examiner

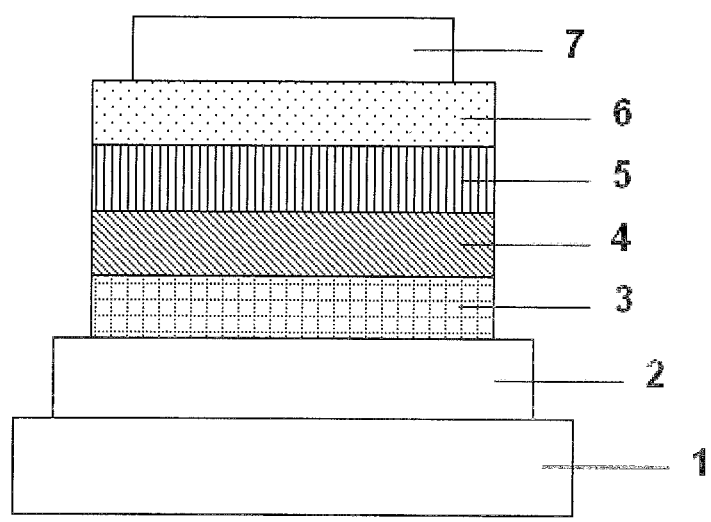

ORGANIC-ELECTROLUMINESCENT-ELEMENT MATERIAL, AND ORGANIC ELECTROLUMINESCENT ELEMENT USING SAME

TECHNICAL FIELD

The present invention relates to an organic electroluminescent device using a carborane compound as a material for an organic electroluminescent device, and more specifically, to a thin film-type device that emits light by applying an electric field to a light-emitting layer containing an organic compound.

BACKGROUND ART

In general, an organic electroluminescent device (hereinafter referred to as organic EL device) includes a light-emitting layer and a pair of counter electrodes interposing the light-emitting layer therebetween in its simplest structure. That is, the organic EL device uses the phenomenon that, when an electric field is applied between both the electrodes, electrons are injected from a cathode and holes are injected from an anode, and each electron and each hole recombine in the light-emitting layer to emit light.

In recent years, progress has been made in developing an organic EL device using an organic thin film. In order to enhance luminous efficiency particularly, the optimization of the kind of electrodes has been attempted for the purpose of improving the efficiency of injection of carriers from the electrodes. As a result, there has been developed a device in which a hole-transporting layer formed of an aromatic diamine and a light-emitting layer formed of an 8-hydroxyquinoline aluminum complex ($Alq_3$) are formed between electrodes as thin films, resulting in a significant improvement in luminous efficiency, as compared to related-art devices in which a single crystal of anthracene or the like is used. Thus, the development of the above-mentioned organic EL device has been promoted in order to accomplish its practical application to a high-performance flat panel having features such as self-luminescence and rapid response.

Further, investigations have been made on using phosphorescent light rather than fluorescent light as an attempt to raise the luminous efficiency of a device. Many kinds of devices including the above-mentioned device in which a hole-transporting layer formed of an aromatic diamine and a light-emitting layer formed of $Alq_3$ are formed emit light by using fluorescent light emission. However, by using phosphorescent light emission, that is, by using light emission from a triplet excited state, luminous efficiency is expected to be improved by from about three times to about four times, as compared to the case of using related-art devices in which fluorescent light (singlet) is used. In order to accomplish this purpose, investigations have been made on adopting a coumarin derivative or a benzophenone derivative as a light-emitting layer, but extremely low luminance has only been provided. Further, investigations have been made on using a europium complex as an attempt to use a triplet state, but highly efficient light emission has not been accomplished. In recent years, many investigations have been made mainly on an organic metal complex, for example, an iridium complex for the purpose of attaining high luminous efficiency and a long lifetime, as disclosed in Patent Literature 1.

CITATION LIST

Patent Literature

[PTL 1] WO 01/041512 A1
[PTL 2] JP 2001-313178 A
[PTL 3] JP 2005-162709 A
[PTL 4] JP 2005-166574 A
[PTL 5] US 2012/0319088 A1
[PTL 6] WO 2013/094834 A1

Non Patent Literature

[NPL 1] J. Am. Chem. Soc. 2012, 134, 17982-17990
[NPL 2] J. Am. Chem. Soc. 2010, 132, 6578-6587

In order to obtain high luminous efficiency, host materials that are used with the dopant materials described above play an important role. A typical example of the host materials proposed is 4,4'-bis(9-carbazolyl)biphenyl (CBP) as a carbazole compound disclosed in Patent Literature 2. When CBP is used as a host material for a green phosphorescent light-emitting material typified by a tris(2-phenylpyridine) iridium complex ($Ir(ppy)_3$), the injection balance between charges is disturbed because CBP has the characteristic of facilitating the delivery of holes and not facilitating the delivery of electrons. Thus, excessively delivered holes flow out into an electron-transporting layer side, with the result that the luminous efficiency from $Ir(ppy)_3$ lowers.

As described above, in order to provide high luminous efficiency to an organic EL device, it is necessary to use a host material that has high triplet excitation energy, and is striking a good balance in both charge (hole and electron)-injecting/transporting properties. Further desired is a compound that is electrochemically stable and has high heat resistance and excellent amorphous stability, and hence further improvement has been demanded.

In Patent Literatures 3, 4, 5, and 6, and Non Patent Literatures 1 and 2, there are disclosures of carborane compounds shown below.

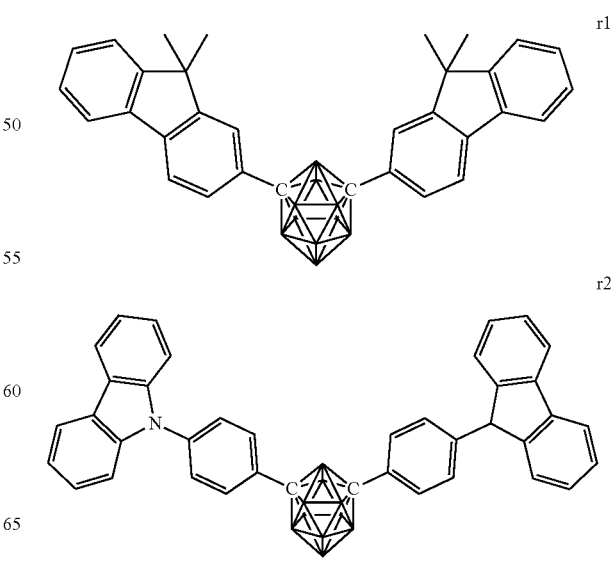

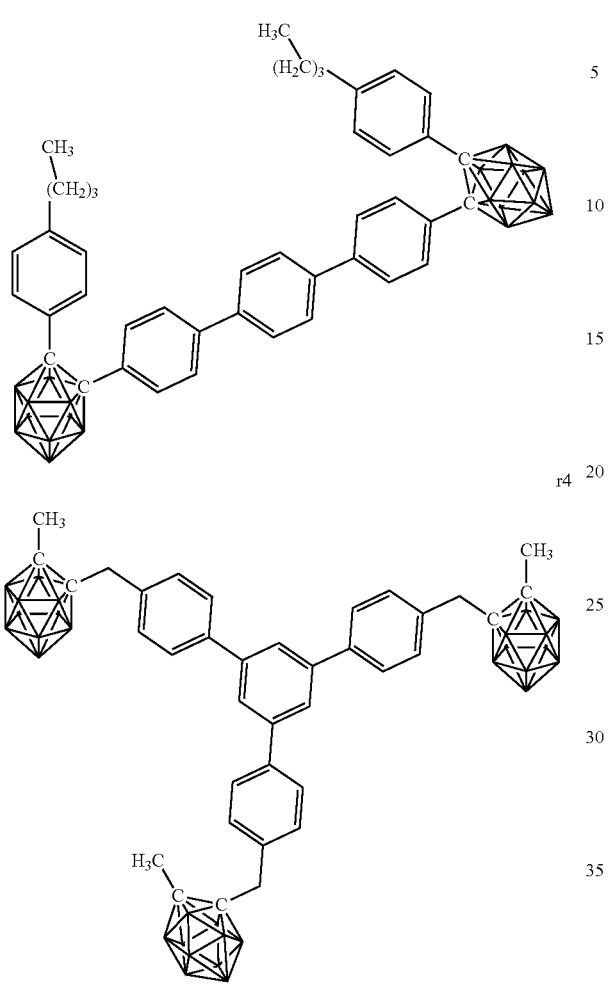

However, in each of the literatures, there is no teaching of the usefulness of a carborane compound in which a boron atom of a carborane ring is substituted with an aromatic group.

SUMMARY OF INVENTION

In order to apply an organic EL device to a display device in a flat panel display or the like, it is necessary to improve the luminous efficiency of the device and also to ensure sufficiently the stability in driving the device. The present invention has an object to provide, in view of the above-mentioned circumstances, an organic EL device that has high efficiency and high driving stability and is practically useful and a compound suitable for the organic EL device.

The inventors of the present invention have made extensive investigations, and as a result, have found that the use of a carborane compound in which a boron atom of a carborane ring is substituted with an aromatic group in an organic EL device enables the device to show excellent characteristics. Thus, the inventors have completed the present invention.

The present invention is directed to a material for an organic electroluminescent device, including a carborane compound represented by the following general formula (1).

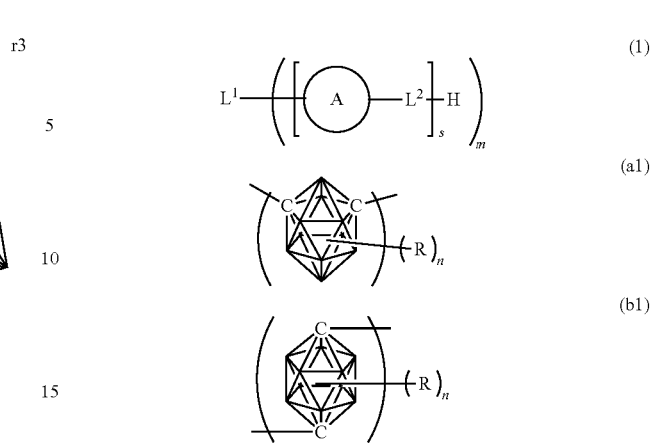

In the formulae, a ring A represents a divalent carborane group represented by the formula (a1) or the formula (b1), and when a plurality of the rings A are present in a molecule thereof, the plurality of the rings A may be identical to or different from each other, a represents a number of repetitions and represents an integer of 1 or 2, and m represents a substitution number and m represents an integer of from 1 to 4, provided that when m=2, s=1.

$L^1$ represents a single bond, an m-valent substituted or unsubstituted aromatic hydrocarbon group having 6 to 30 carbon atoms, an m-valent substituted or unsubstituted aromatic heterocyclic group having 3 to 30 carbon atoms, or an m-valent linked aromatic group formed by linking 2 to 6 aromatic rings of the aromatic hydrocarbon group or the aromatic heterocyclic group. In a case of the linked aromatic group, the group may be linear or branched, and its aromatic rings to be linked may be identical to or different from each other. In a case except m=2, $L^1$ is free from representing a single bond, and in a case where m=2, $L^3$ represents a group containing at least one aromatic heterocyclic group or a single bond.

Each $L^2$ independently represent a single bond, or a divalent substituted or unsubstituted aromatic hydrocarbon group having 6 to 30 carbon atoms, a divalent substituted or unsubstituted aromatic heterocyclic group having 3 to 30 carbon atoms, or a divalent linked aromatic group formed by linking 2 to 6 aromatic rings of the aromatic hydrocarbon group or the aromatic heterocyclic group. In a case of the linked aromatic group, the group may be linear or branched, and its aromatic rings to be linked may be identical to or different from each other. In addition, $L^2$-H at a terminal may represent an alkyl group having 1 to 12 carbon atoms, an alkoxy group having 1 to 12 carbon atoms, or an acetyl group.

R in each of the formulae (a1) and (b1) represents a substituted or unsubstituted aromatic hydrocarbon group having 6 to 30 carbon atoms, a substituted or unsubstituted aromatic heterocyclic group having 3 to 30 carbon atoms, or a linked aromatic group formed by linking 2 to 6 aromatic rings of the aromatic hydrocarbon group or the aromatic heterocyclic group, and in a case of the linked aromatic group, the group may be linear or branched, and its aromatic rings to be linked may be identical to or different from each other. n represents an integer of 1 or 2.

When a plurality of $L^2$ or R are present in a molecule thereof, the plurality of $L^2$ or R may be identical to or different from each other.

In a preferred embodiment, in the general formula (1), the ring A represents a divalent carborane group represented by the formula (a1). In addition, in a preferred embodiment, the general formula (1) is the following general formula (2).

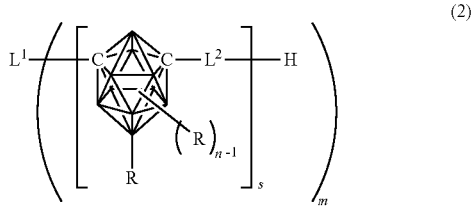

(2)

In the general formula (2), $L^1$, $L^2$, R, s, m, and n each have the same meaning as that in the general formula (1). In addition, $L^1$, $L^2$, or m in the general formula (2) preferably satisfies one or more of the following (1) to (3):
(1) m represents an integer of 1 or 2, preferably an integer of 1;
(2) $L^1$ and $L^2$ each independently represent a substituted or unsubstituted aromatic hydrocarbon group having 6 to 18 carbon atoms, a substituted or unsubstituted aromatic heterocyclic group having 3 to 17 carbon atoms, or a linked aromatic group formed by linking 2 to 6 aromatic rings selected from the aromatic hydrocarbon group and the aromatic heterocyclic group; and
(3) $L^1$ and $L^2$ each independently represent a substituted or unsubstituted aromatic heterocyclic group having 3 to 30 carbon atoms, or a linked aromatic group formed by linking 2 to 6 aromatic rings selected from the aromatic heterocyclic groups.

The present invention is also directed to an organic electroluminescent device having a structure in which an anode, an organic layer, and a cathode are laminated on a substrate, the organic layer including an organic layer containing the above-mentioned material for an organic electroluminescent device.

It is preferred that the organic layer containing the material for an organic electroluminescent device include at least one layer selected from the group consisting of a light-emitting layer, an electron-transporting layer, and a hole-blocking layer, or include a light-emitting layer containing a phosphorescent light-emitting dopant. When the phosphorescent light-emitting dopant is contained, an emission wavelength of the phosphorescent light-emitting dopant preferably has an emission maximum wavelength at 550 nm or less.

A material for a phosphorescent device of the present invention has a structure in which a boron atom on a carborane skeleton is substituted with an aromatic group. A carborane compound having such structural feature enables high-level control of the electron-injecting/transporting properties of a device because its lowest unoccupied molecular orbital (LUMO) that affects the electron-injecting/transporting properties is widely distributed in the entirety of a molecule thereof. Further, the compound enables efficient light emission from a dopant because the compound has the lowest triplet excitation energy (T1 energy) high enough to confine the T1 energy of the dopant. By virtue of the foregoing features, the use of the compound in an organic EL device can achieve a reduction in driving voltage of the device and high luminous efficiency.

In addition, an organic EL device using the material for an organic electroluminescent device of the present invention has a long driving lifetime and durability at a practical level because the material shows a satisfactory amorphous characteristic and high thermal stability, and at the same time, is extremely stable in an excited state.

BRIEF DESCRIPTION OF DRAWINGS

FIG. 1 is a sectional view for illustrating one structural example of an organic EL device.

DESCRIPTION OF EMBODIMENTS

A material for an organic electroluminescent device of the present invention is a carborane compound represented by the general formula (1) or (2). The carborane compound exhibits such excellent effects as described above probably because the compound has a structure in which a boron atom on a carborane skeleton is substituted with an aromatic group. The same symbols in the general formulae (1) and (2) have the same meaning.

$L^1$ represents a single bond, an m-valent substituted or unsubstituted aromatic hydrocarbon group having 6 to 30 carbon atoms, an m-valent substituted or unsubstituted aromatic heterocyclic group having 3 to 30 carbon atoms, or an m-valent linked aromatic group formed by linking 2 to 6 aromatic rings of the aromatic hydrocarbon group or the aromatic heterocyclic group. In the case of the linked aromatic group, the group may be linear or branched, and its aromatic rings to be linked may be identical to or different from each other. The same holds true for the case where $L^2$ or R represents a linked aromatic group. However, when m=2, $L^1$ may represent a single bond, and when $L^1$ represents a group except a single bond, the group is the above-mentioned aromatic heterocyclic group or the above-mentioned linked aromatic group containing at least one aromatic heterocycle.

Each $L^2$ represent a single bond, or a divalent substituted or unsubstituted aromatic hydrocarbon group having 6 to 30 carbon atoms, a divalent substituted or unsubstituted aromatic heterocyclic group having 3 to 30 carbon atoms, or a divalent linked aromatic group formed by linking 2 to 6 aromatic rings of the aromatic hydrocarbon group or the aromatic heterocyclic group, and $L^2$-H at a terminal may represent an alkyl group having 1 to 12 carbon atoms, an alkoxy group having 1 to 12 carbon atoms, or an acetyl group.

Here, a ring A represents a divalent carborane group represented by the formula (a1) or the formula (b1), and when a plurality of rings A are present in a molecule thereof, the rings may be identical to or different from each other. Of the carborane groups, a carborane group represented by the formula (a1) is preferred.

R represents a substituted or unsubstituted aromatic hydrocarbon group having 6 to 30 carbon atoms, a substituted or unsubstituted aromatic heterocyclic group having 3 to 30 carbon atoms, or a linked aromatic group formed by linking 2 to 6 aromatic rings of the aromatic hydrocarbon group or the aromatic heterocyclic group. R is bonded to a boron atom forming a carborane ring. Although an unsubstituted divalent carborane group is represented by $C_2B_{10}H_{10}$, a divalent carborane group substituted with R is represented by $C_2B_{10}H_{10-n}R_n$. Here, n represents 1 or 2.

In each of the general formulae (1) and (2), a represents a number of repetitions, and represents an integer of 1 or 2, preferably an integer of 1.

m represents a substitution number, and represents an integer of from 1 to 4, preferably an integer of 1 or 2, provided that when m=2, s=1.

A case in which $L^1$, $L^2$, or R represents an aromatic hydrocarbon group, an aromatic heterocyclic group, or a linked aromatic group is described. In the case of any such group, $L^1$ represents an m-valent group, $L^2$ represents a divalent group, and R represents a monovalent group.

Specific examples of the unsubstituted aromatic hydrocarbon group include groups each produced by removing a hydrogen atom from an aromatic hydrocarbon compound, such as benzene, naphthalene, fluorene, anthracene, phenanthrene, triphenylene, tetraphenylene, fluoranthene, pyrene, or chrysene. Of those, a group produced by removing a hydrogen atom from benzene, naphthalene, fluorene, phenanthrene, or triphenylene is preferred.

Specific examples of the unsubstituted aromatic heterocyclic group include linked groups each produced by removing a hydrogen atom from an aromatic heterocyclic compound, such as pyridine, pyrimidine, triazine, quinoline, isoquinoline, quinoxaline, quinazoline, naphthyridine, carbazole, dibenzofuran, dibenzothiophene, acridine, azepine, tribenzazepine, phenazine, phenoxazine, phenothiazine, dibenzophosphole, or dibenzoborole. Of those, a group produced by removing a hydrogen atom from pyridine, pyrimidine, triazine, carbazole, quinazoline, dibenzofuran, or dibenzothiophene is preferred.

The term "linked aromatic group" as used herein refers to a group produced by removing a hydrogen atom from an aromatic compound in which a plurality of aromatic rings of aromatic hydrocarbon compounds or aromatic heterocyclic compounds are linked to each other by single bonding. The linked aromatic group is a group formed by linking 2 to 6 aromatic rings, and the aromatic rings to be linked may be identical to or different from each other, and may include both an aromatic hydrocarbon group and an aromatic heterocyclic group. The number of the aromatic rings to be linked is preferably from 2 to 4, more preferably 2 or 3. The number of carbon atoms of each aromatic group forming the linked aromatic group falls within the range of the number of carbon atoms when $L^1$, $L^2$, or R represents an aromatic hydrocarbon group or an aromatic heterocyclic group, and the total number of carbon atoms of the linked aromatic group is desirably 60 or less, preferably 40 or less.

Specific examples of the linked aromatic group include groups each produced by removing a hydrogen atom from biphenyl, terphenyl, quaterphenyl, phenylnaphthalene, diphenylnaphthalene, phenylanthracene, diphenylanthracene, diphenylfluorene, bipyridine, bipyrimidine, bitriazine, biscarbazole, bisdibenzofuran, bisdibenzothiophene, phenylpyridine, phenylpyrimidine, phenyltriazine, phenylcarbazole, phenyldibenzofuran, diphenylpyridine, diphenyltriazine, bis(carbazolyl)benzene, bisdibenzofuranylbenzene, or the like.

The aromatic hydrocarbon group, the aromatic heterocyclic group, or the linked aromatic group may have a substituent, and when any such group has a substituent, the substituent is preferably a diarylamino group having 1 to 30 carbon atoms, an alkyl group having 1 to 12 carbon atoms, an alkoxy group having 1 to 12 carbon atoms, or an acetyl group. The substituent is more preferably a diarylamino group having 1 to 30 carbon atoms, an alkyl group having 1 to 4 carbon atoms, an alkoxy group having 1 or 2 carbon atoms, or an acetyl group. In this description, the number of carbon atoms of the substituent is construed as being included in the calculation of the number of carbon atoms. However, the total number of carbon atoms including the number of carbon atoms of the substituent preferably satisfies the above-mentioned number of carbon atoms.

Here, when the linked aromatic group is a divalent group, the group is represented by, for example, any one of the following formulae, and its aromatic rings may be linked in a linear manner or a branched manner.

$$—Ar^1—Ar^2—Ar^3 \quad —Ar^1—\underset{\underset{Ar^5}{|}}{\overset{\overset{Ar^4}{|}}{Ar^2}}—Ar^3 \quad —Ar^1—\underset{\underset{Ar^6}{|}}{\overset{\overset{Ar^4}{|}}{Ar^2}}—Ar^3$$

$Ar^1$ to $Ar^6$ each represent a substituted or unsubstituted aromatic hydrocarbon ring or aromatic heterocycle.

The case in which $L^2$-H at the terminal represents an alkyl group or an alkoxy group is described.

The alkyl group may be saturated or unsaturated, and may be linear, branched, or cyclic, and preferred specific examples thereof include: alkyl groups each having 1 to 8 carbon atoms, such as a methyl group, an ethyl group, an ethenyl group, a propyl group, a propenyl group, an isopropyl group, a butyl group, a t-butyl group, a pentyl group, a hexyl group, and an octyl group; and cycloalkyl groups each having 5 to 8 carbon atoms, such as a cyclopentyl group and a cyclohexyl group.

The alkoxy group may be linear or branched, and preferred specific examples thereof include alkoxy groups each having 1 to 8 carbon atoms, such as a methoxy group, an ethoxy group, a propoxy group, an isopropoxy group, a butoxy group, a t-butoxy group, a pentoxy group, a 2-ethylbutoxy group, a hexyloxy group, and an octyloxy group.

The carborane compound represented by the general formula (1) or (2) can be synthesized by using a known approach after the selection of a raw material in accordance with the structure of a target compound.

Compounds (A-1) and (A-2) can be synthesized by the following reaction formulae with reference to synthesis examples disclosed in Inorganic Chemistry, 1995, 34, p 2095-2100.

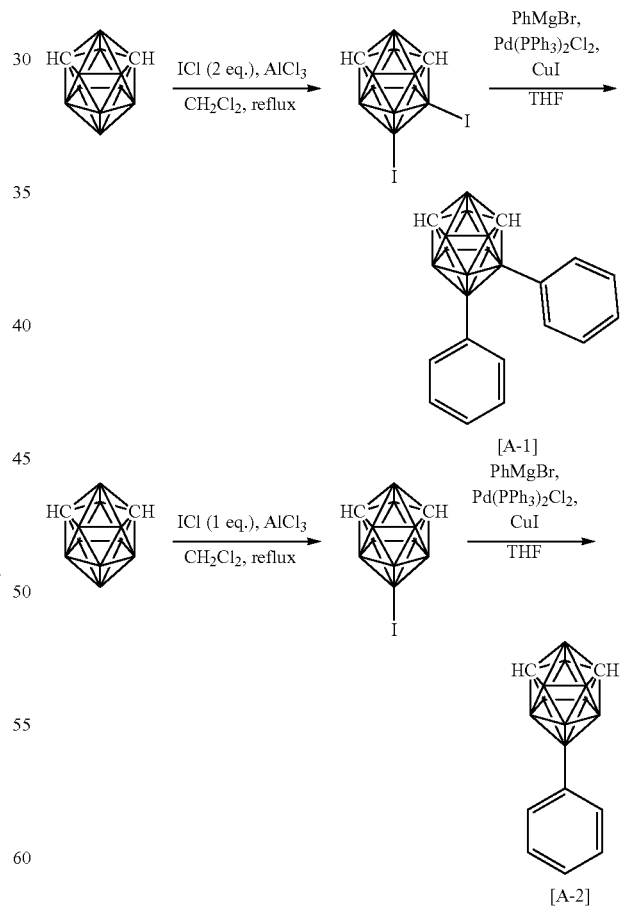

Specific examples of the carborane compound represented by the general formula (1) or (2) are shown below. However, the material for an organic electroluminescent device of the present invention is not limited thereto.

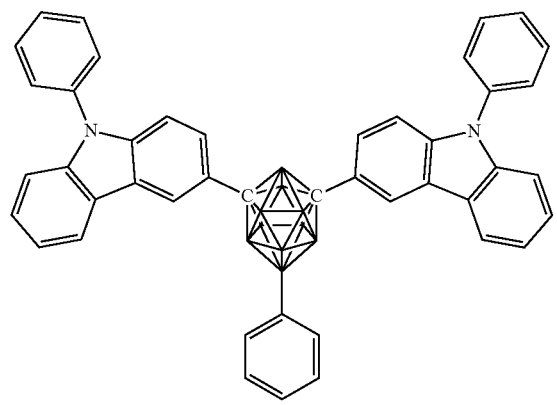
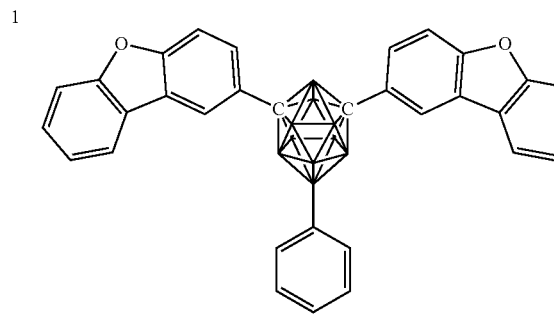
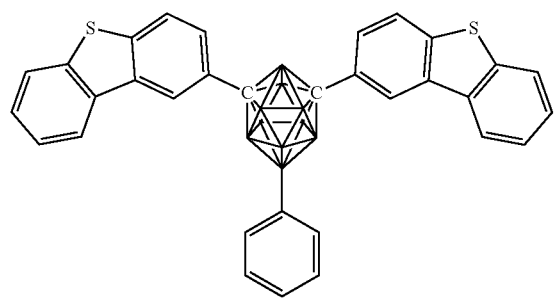
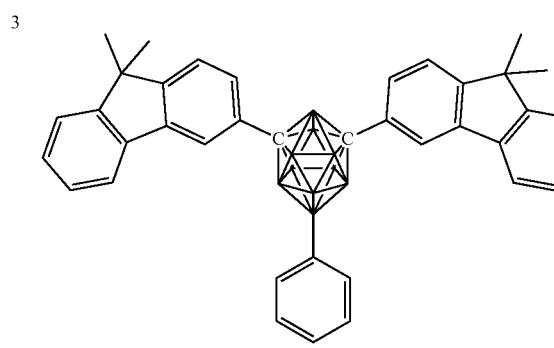
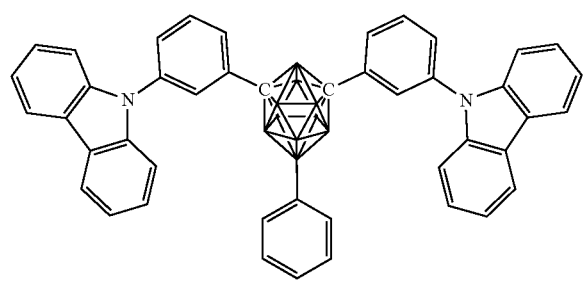
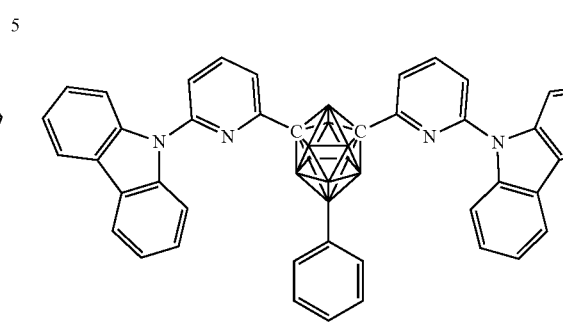
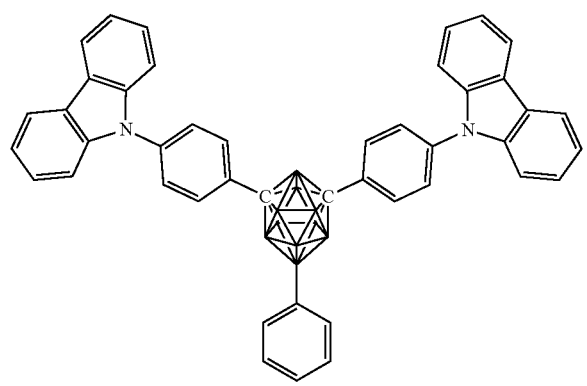
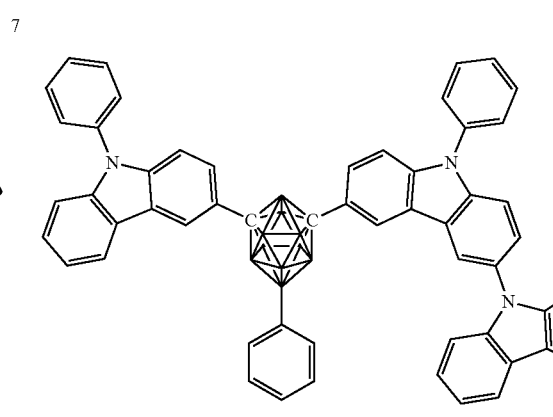

-continued
9
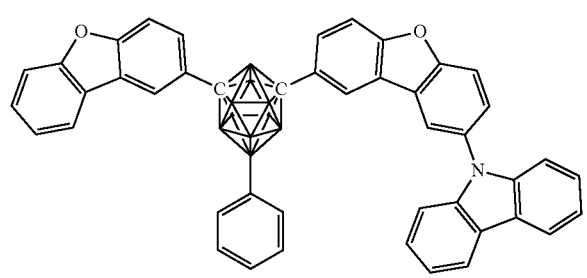
10
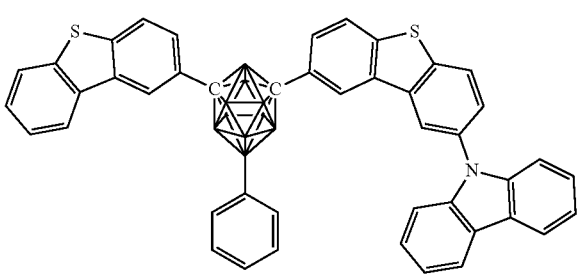
11
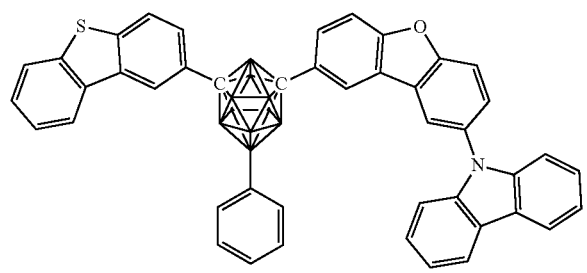
12
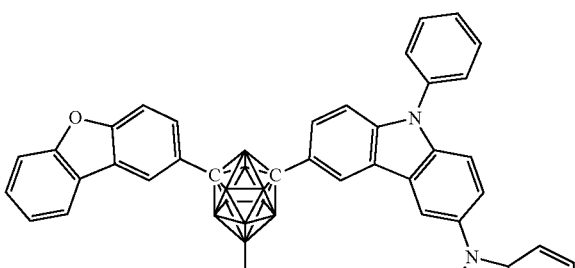
13
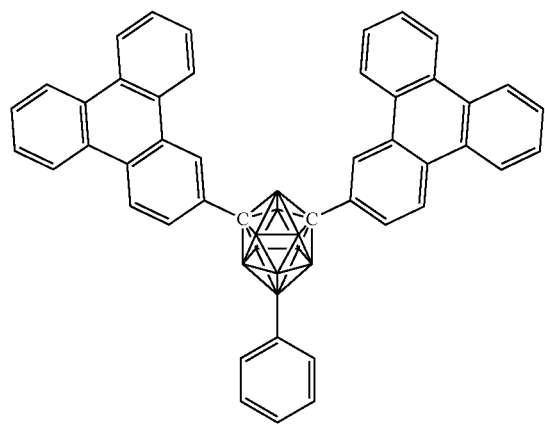
14
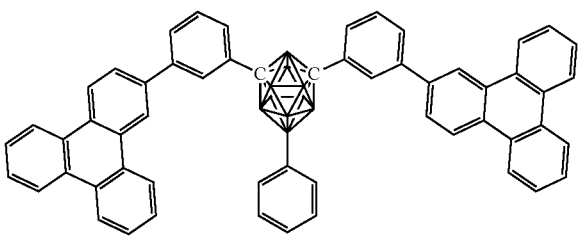
15
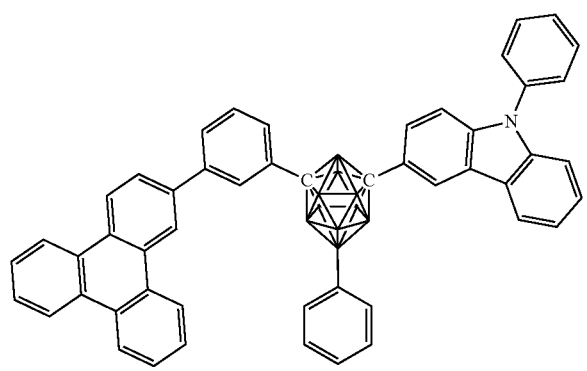
16
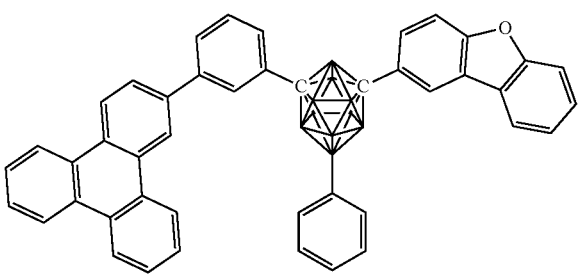

-continued
17
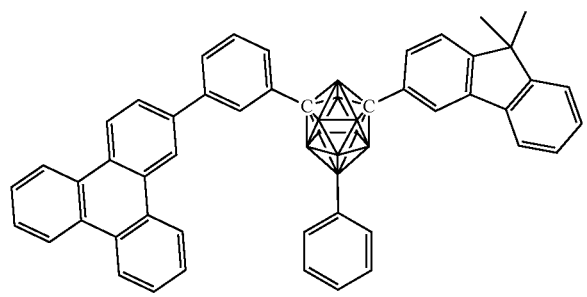
18
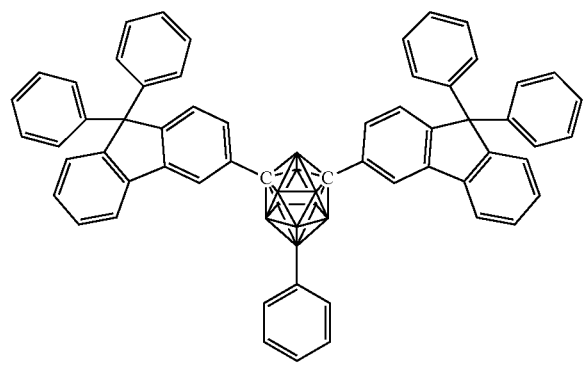
19
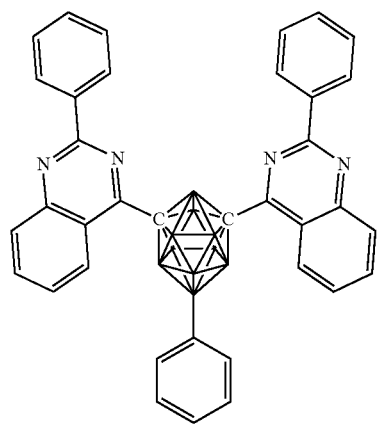
20
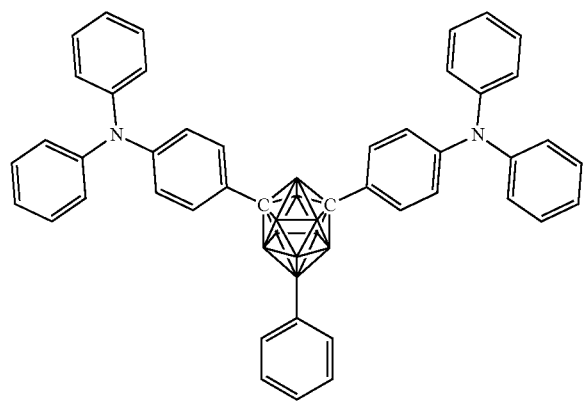
21
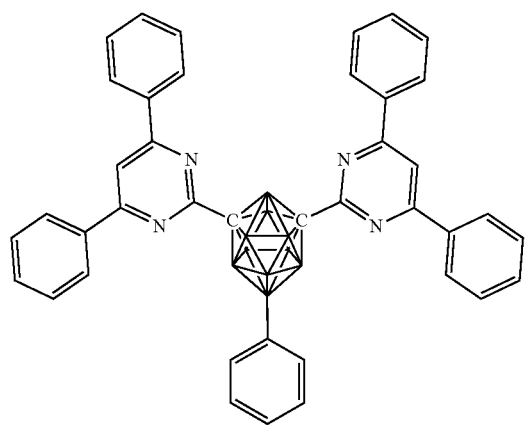
22
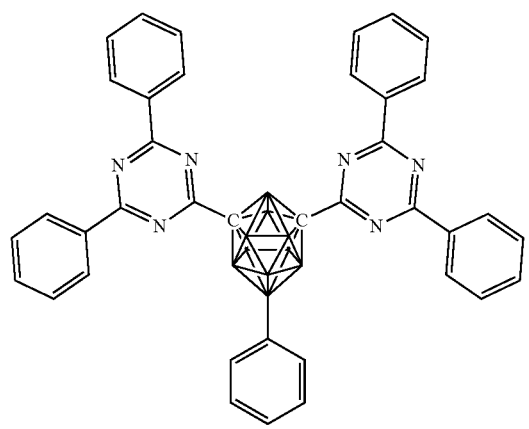

23
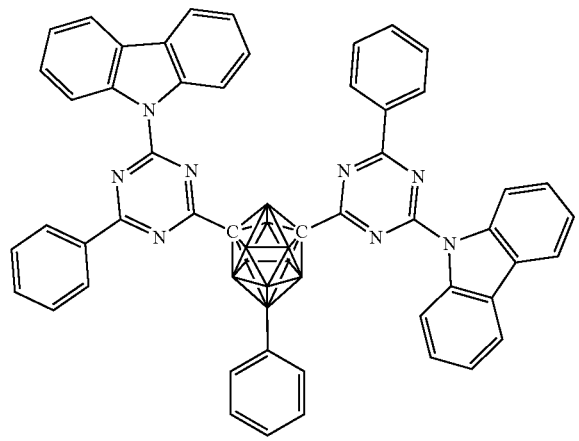
24
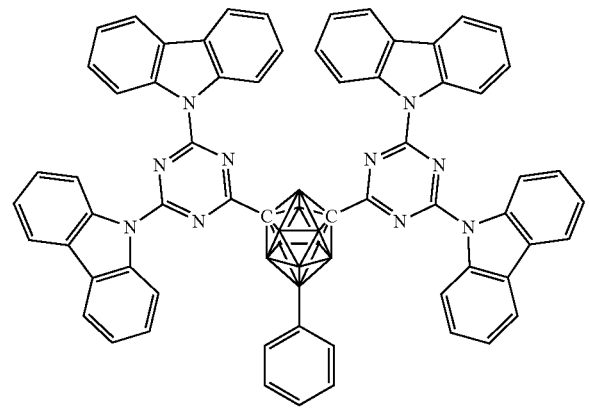
25
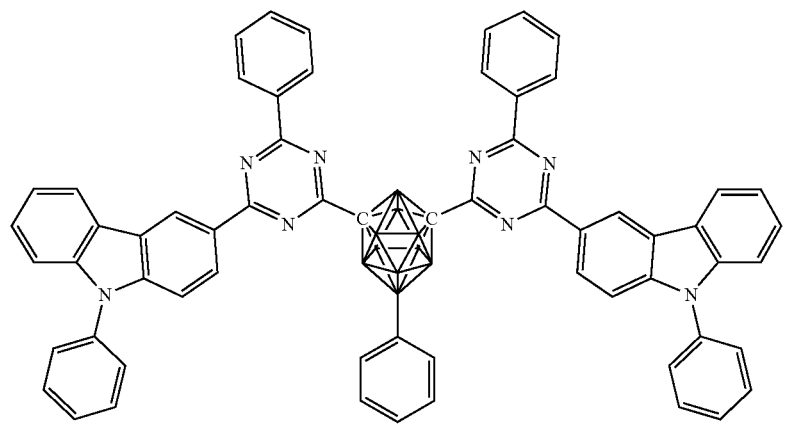
26
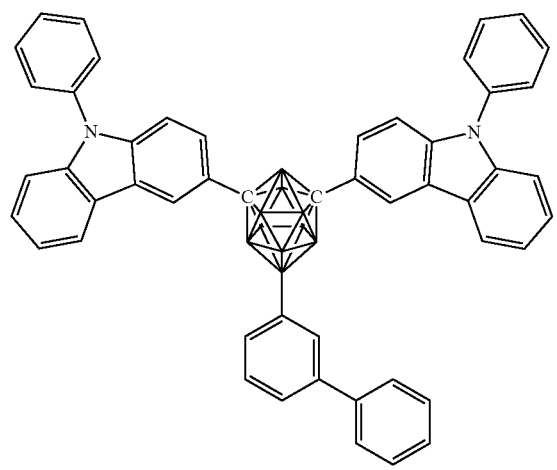
27
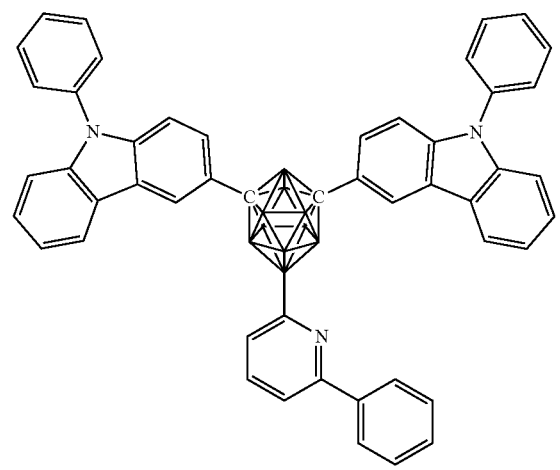

-continued
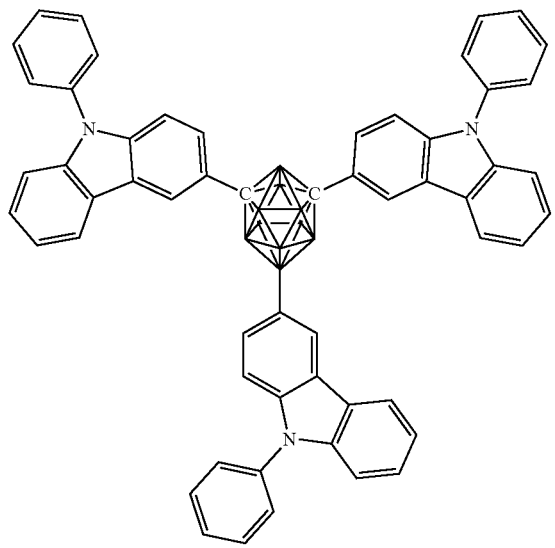
28
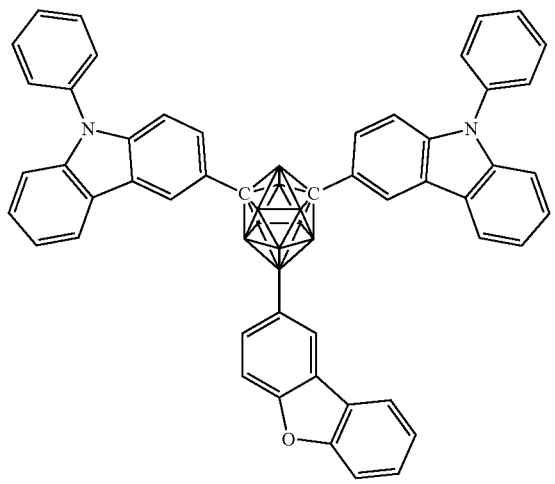
29
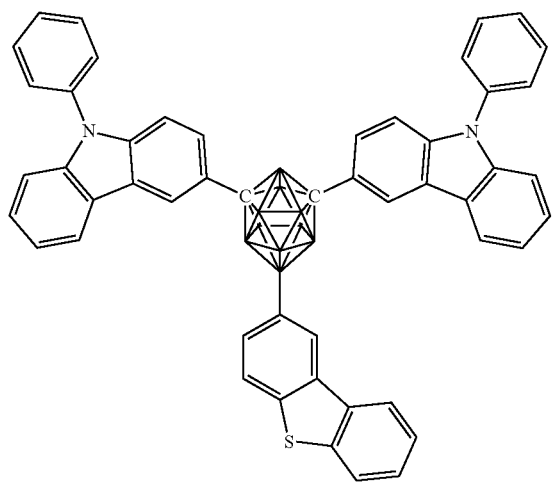
30
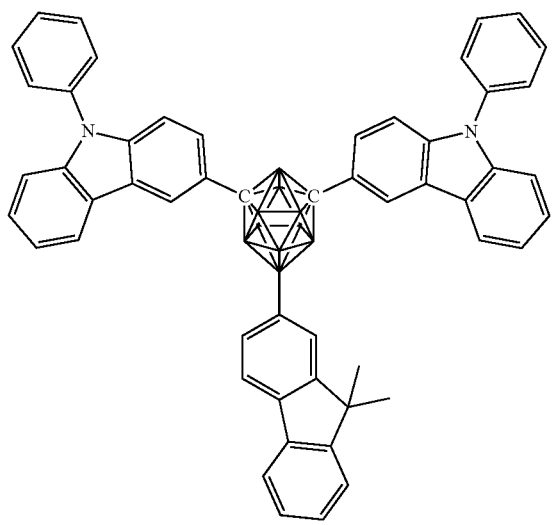
31
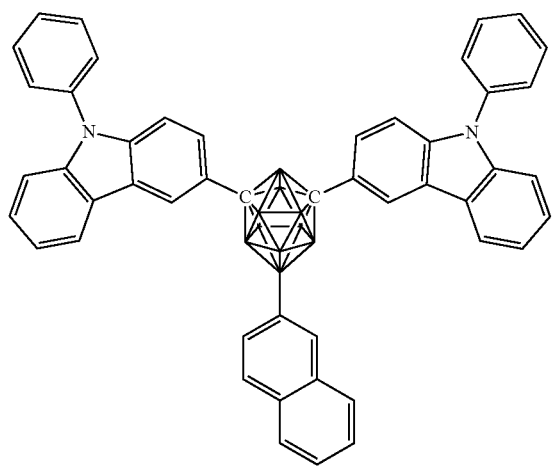
32
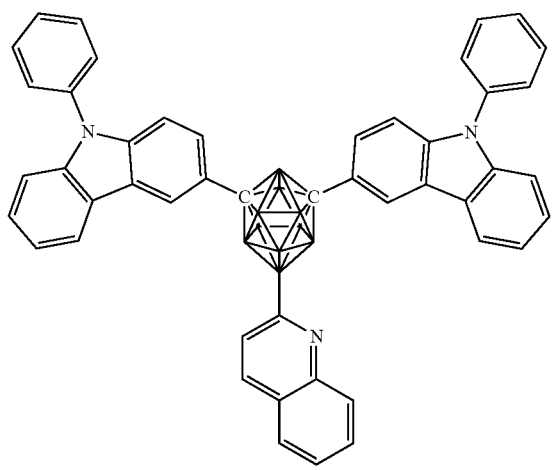
33

-continued
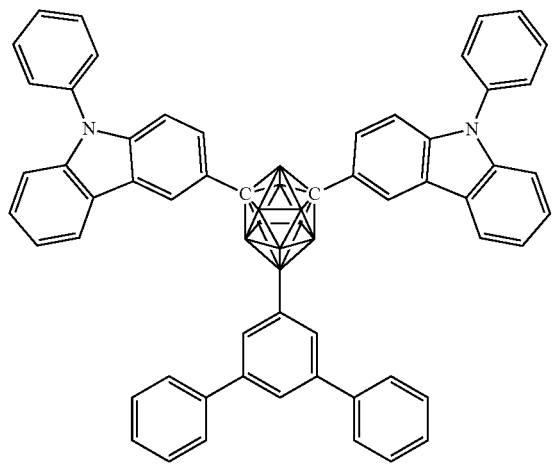
34
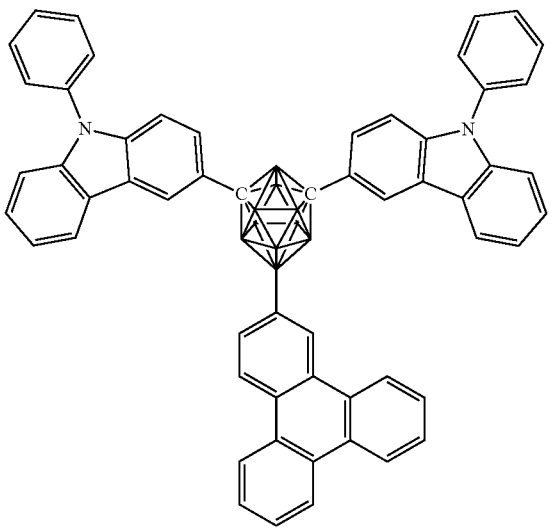
35
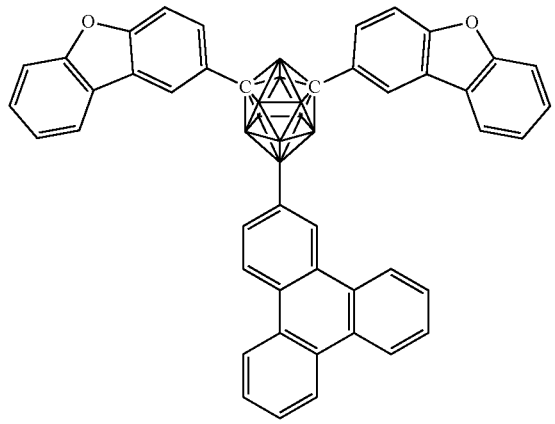
36
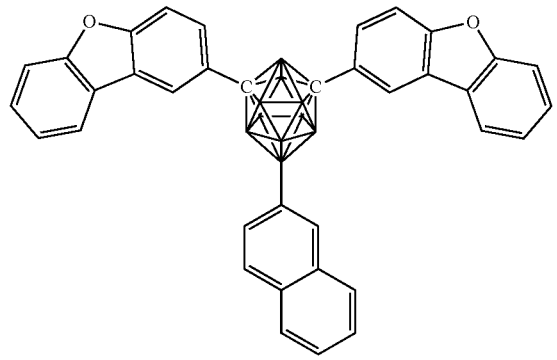
37
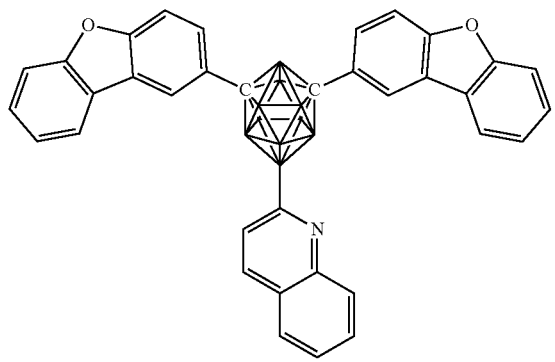
38
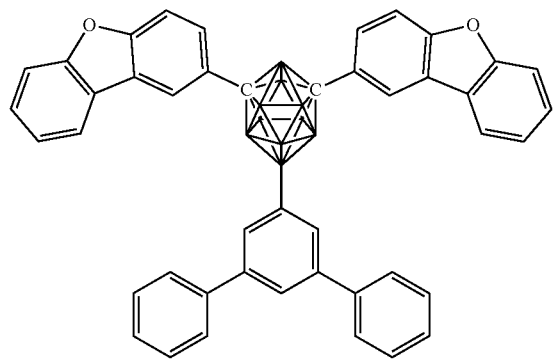
39

-continued
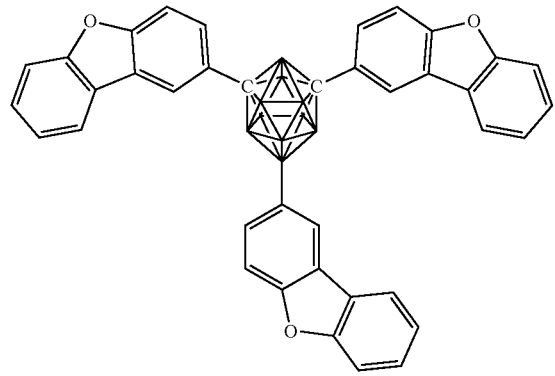
40
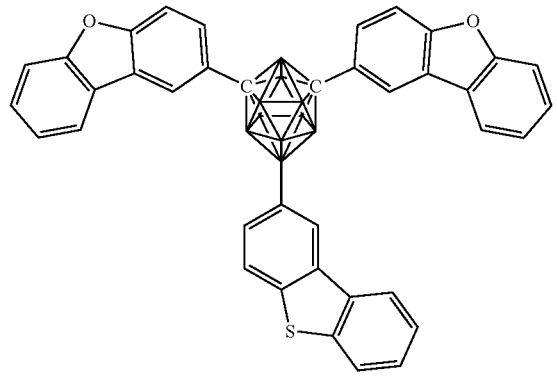
41
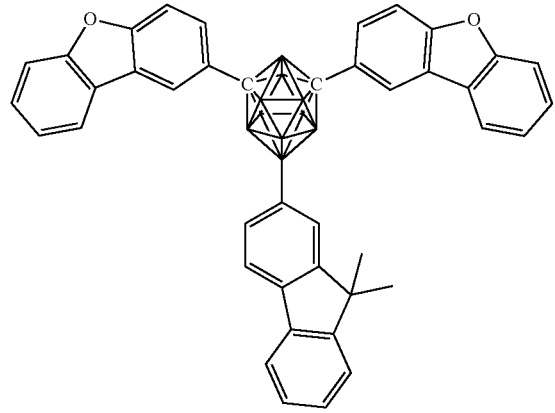
42
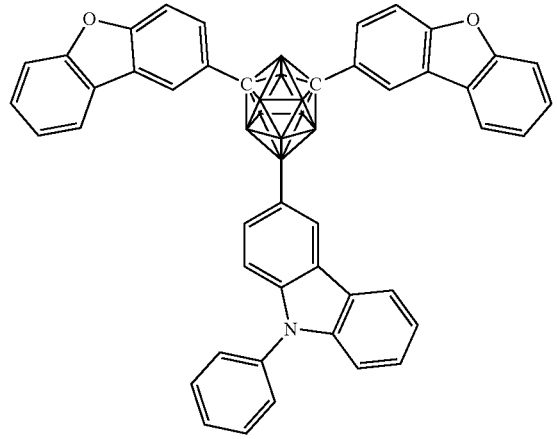
43
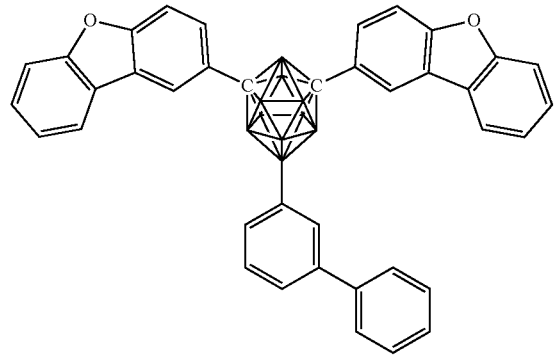
44
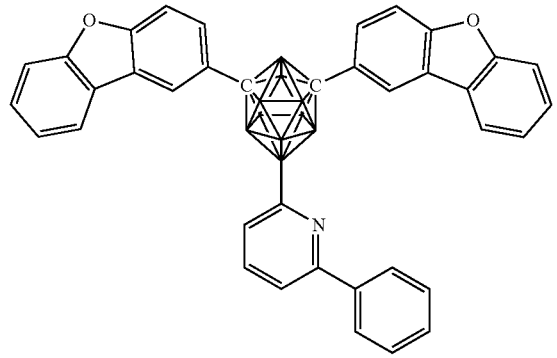
45
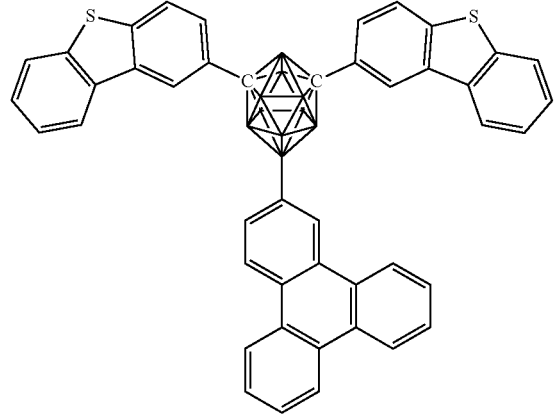
46
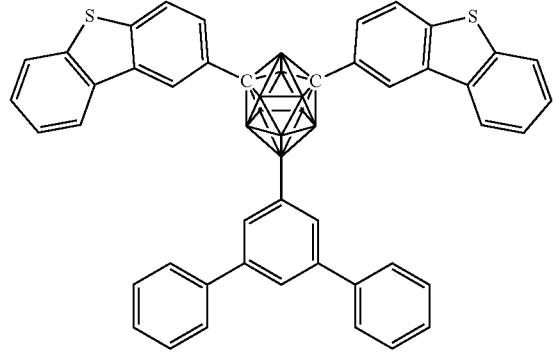
47

-continued
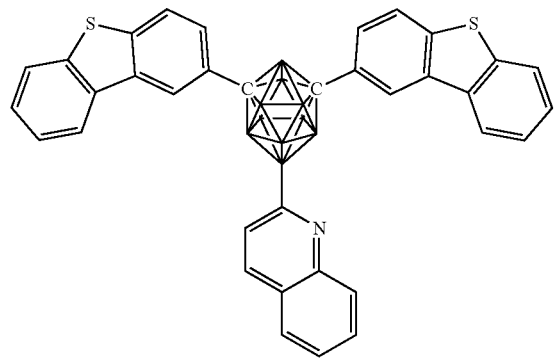
48
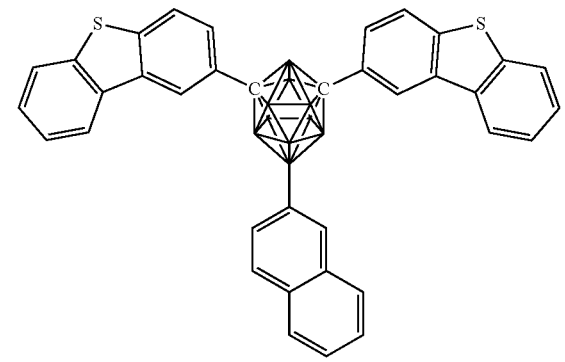
49
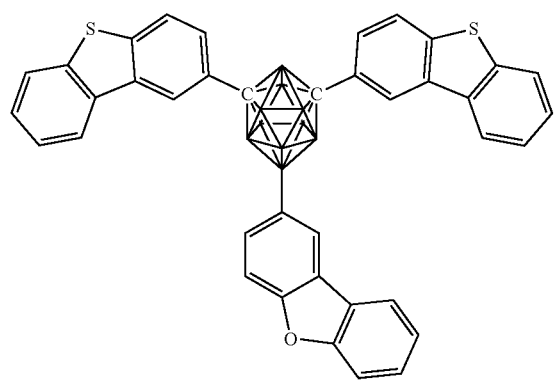
50
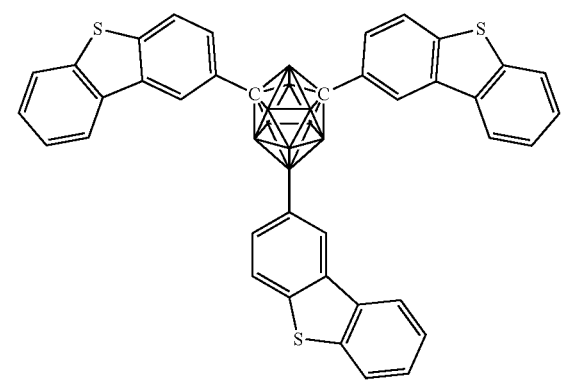
51
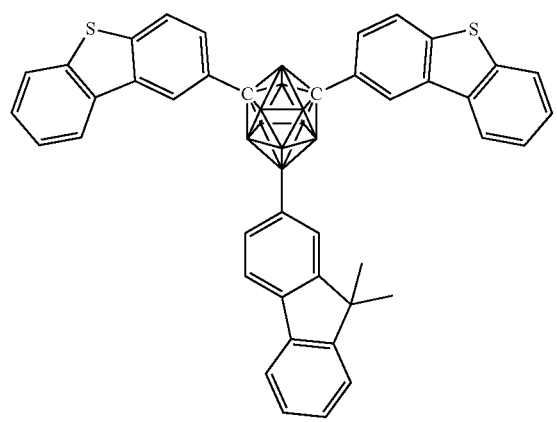
52
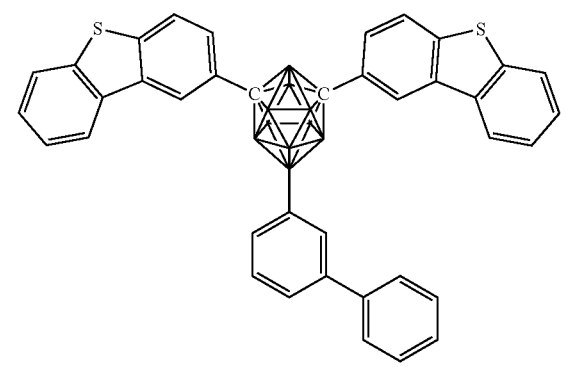
53
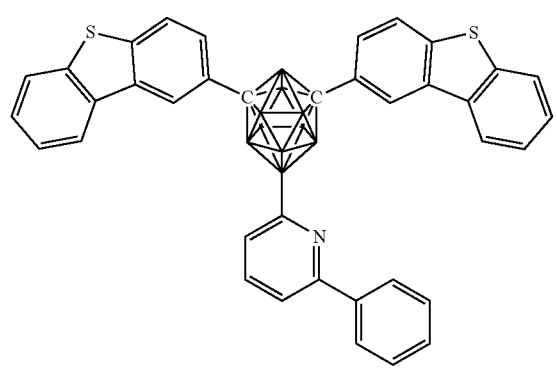
54
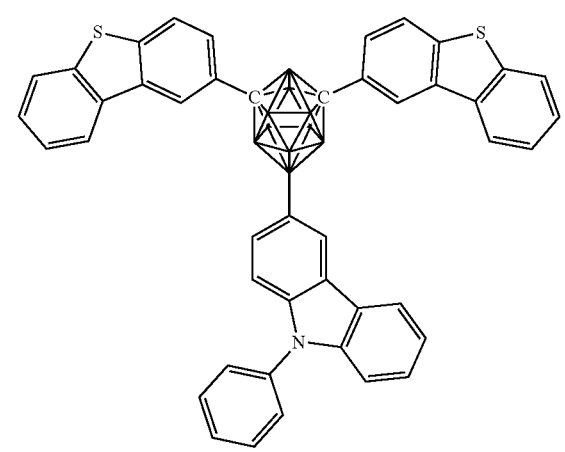
55

-continued
56
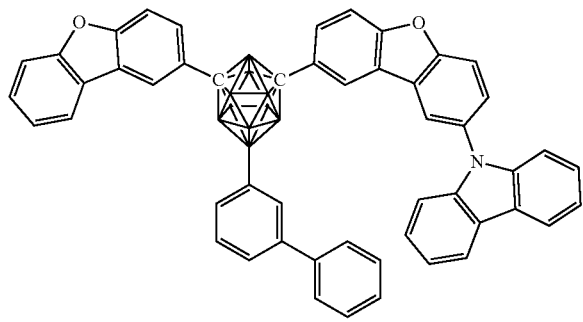
57
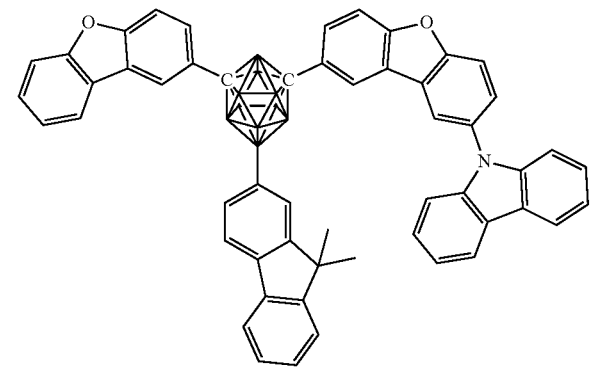
58
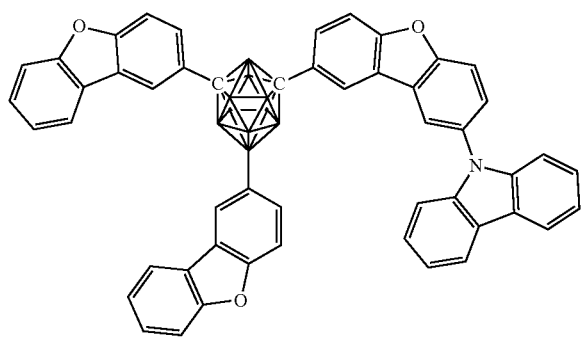
59
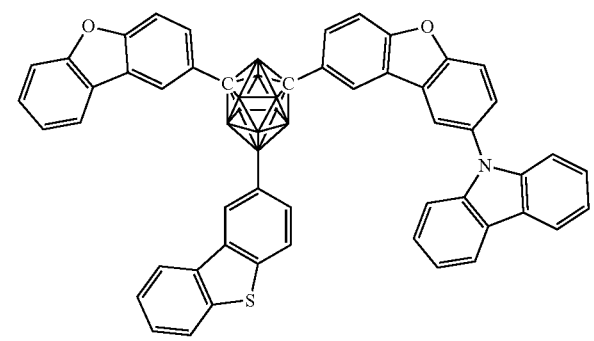
60
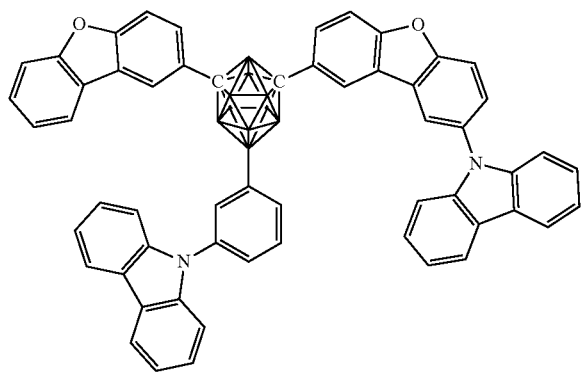
61
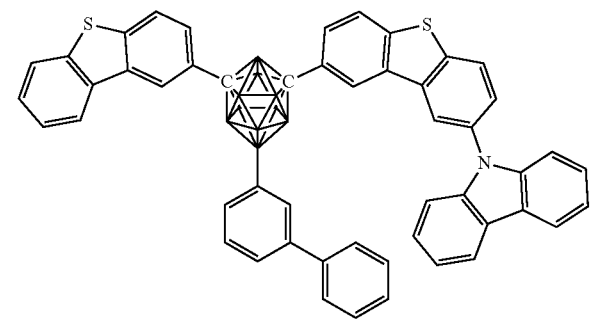
62
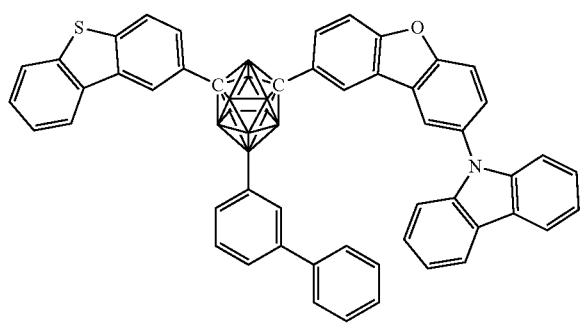
63
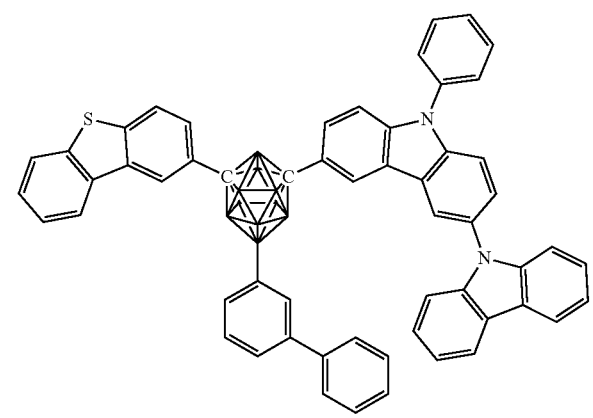

-continued
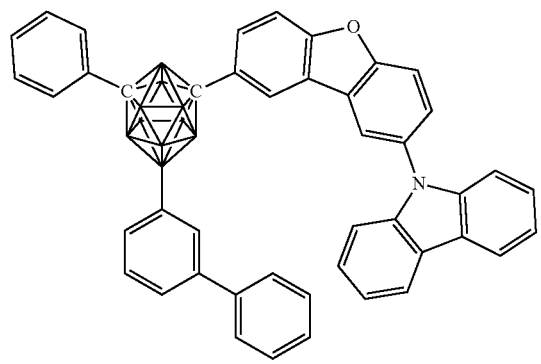
64
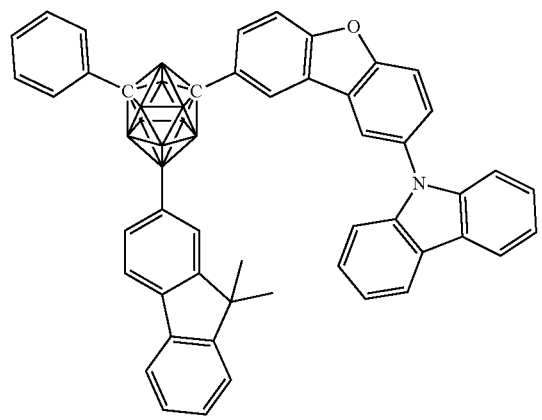
65
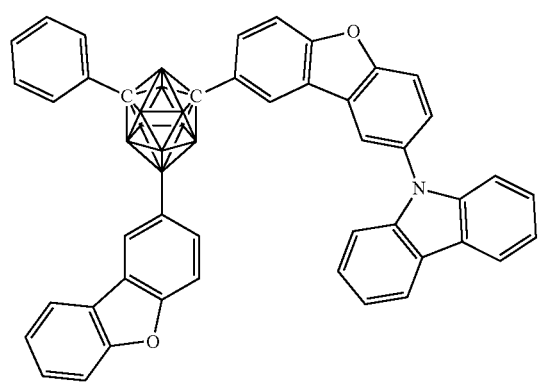
66
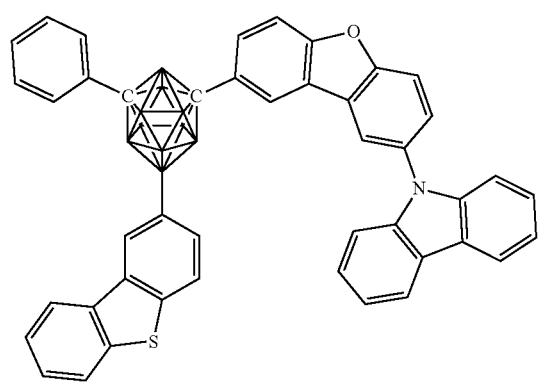
67
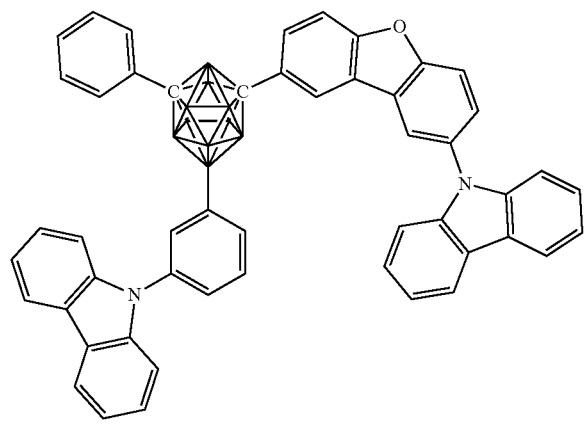
68
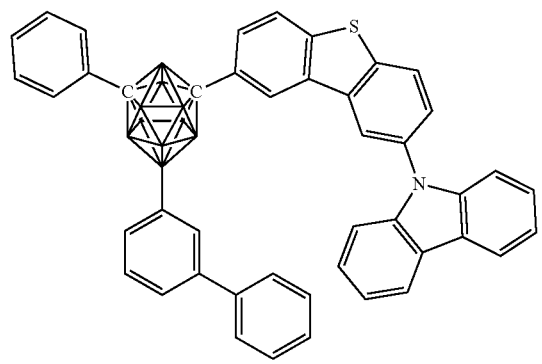
69
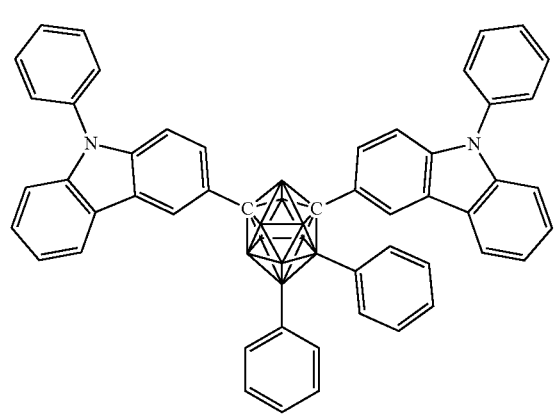
70
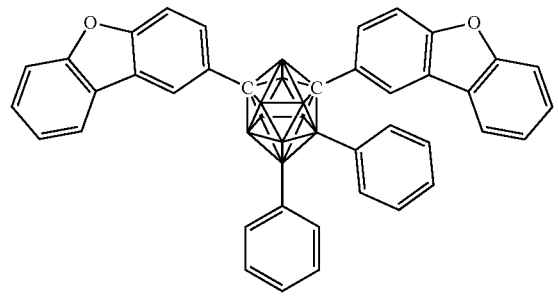
71

-continued
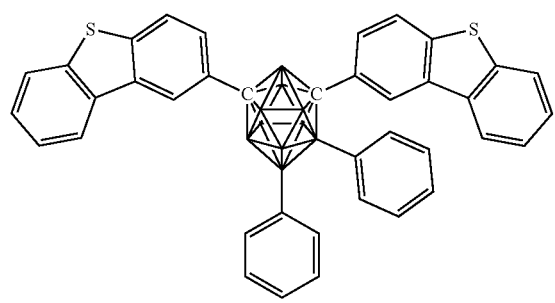
72
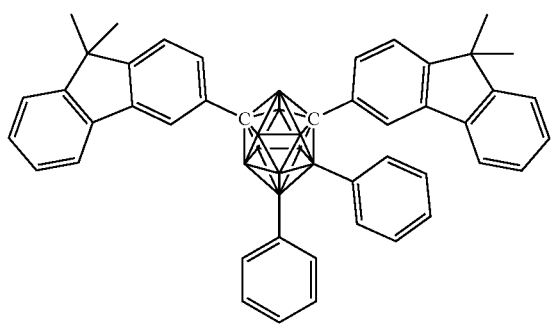
73
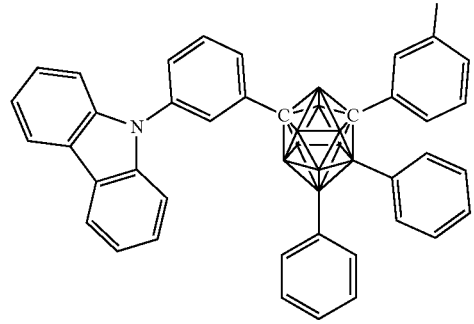
74
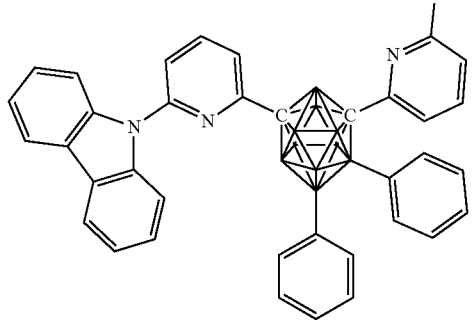
75
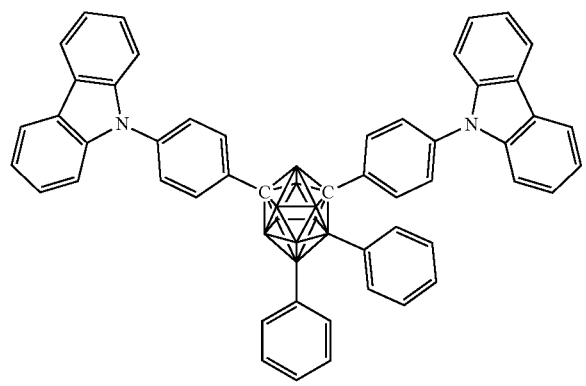
76
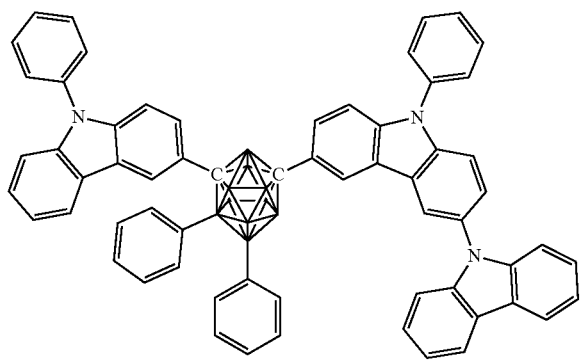
77
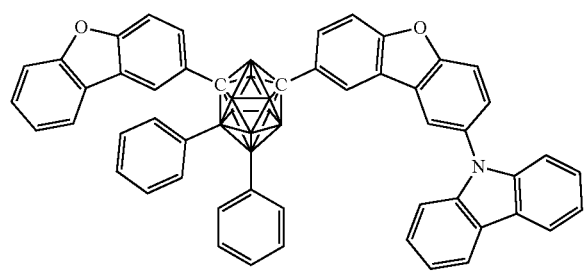
78
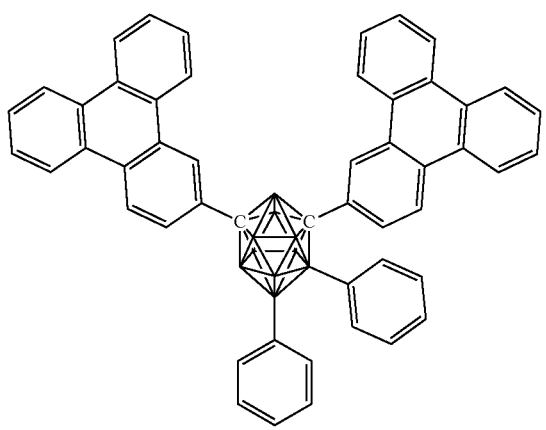
79

-continued
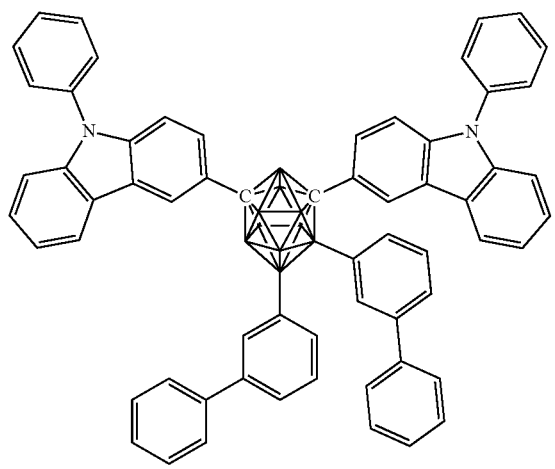
80
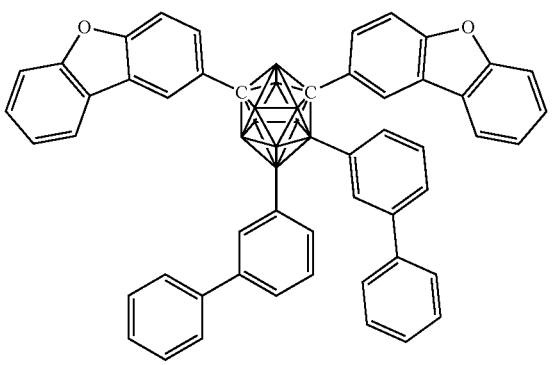
81
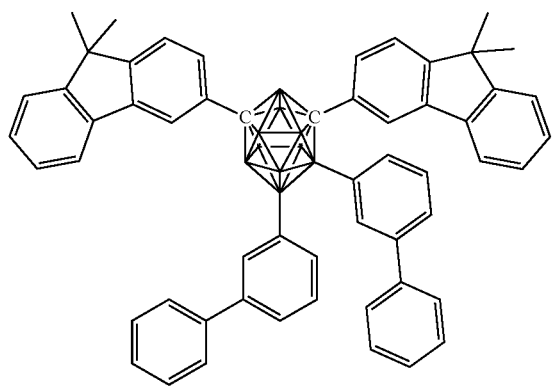
82
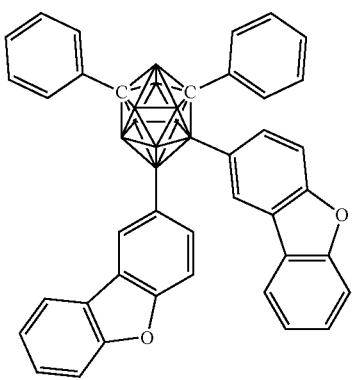
83
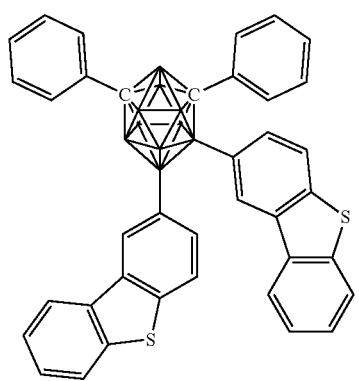
84
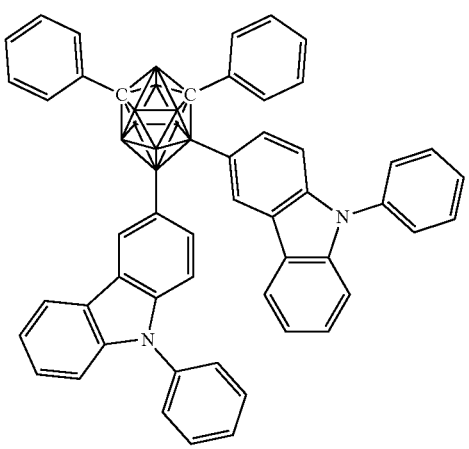
85

86
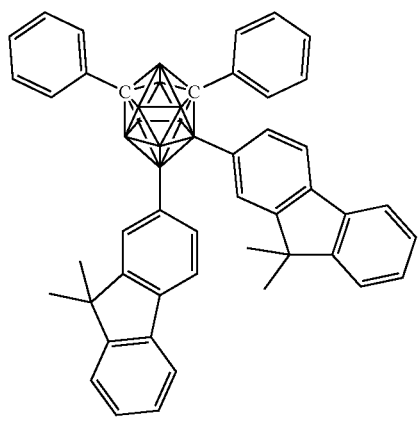
87
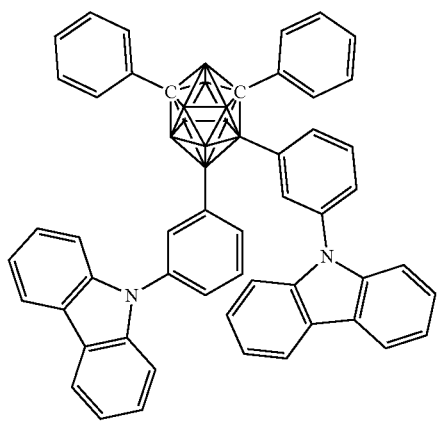
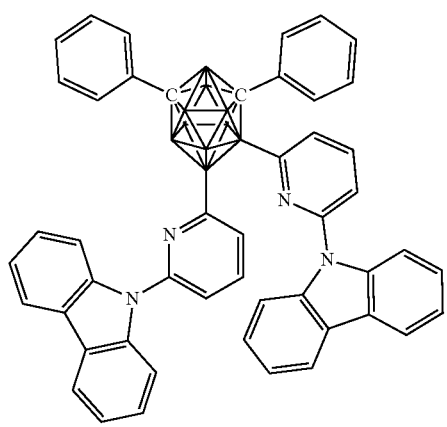
88
89
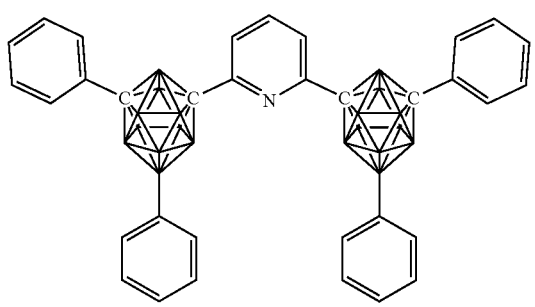
90
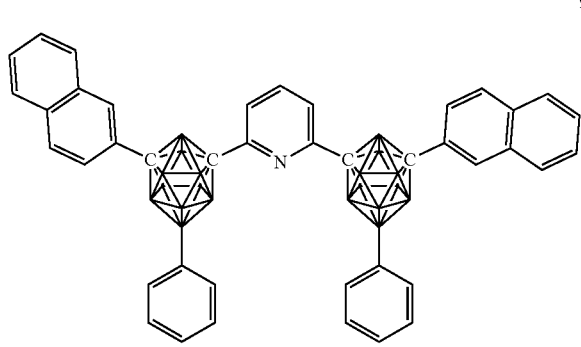
91
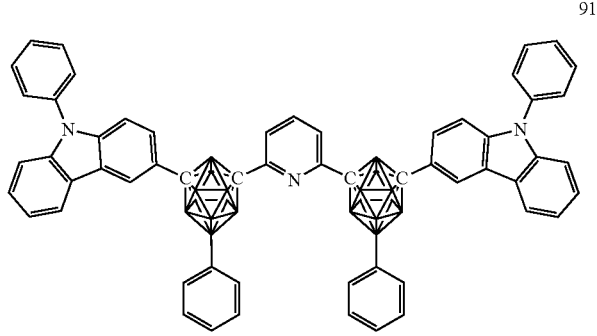

-continued
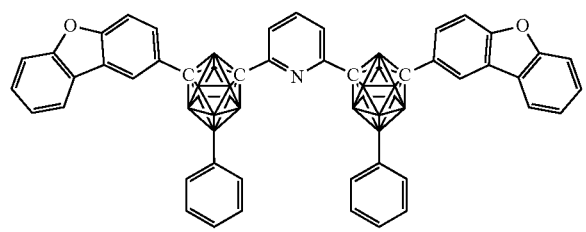
92
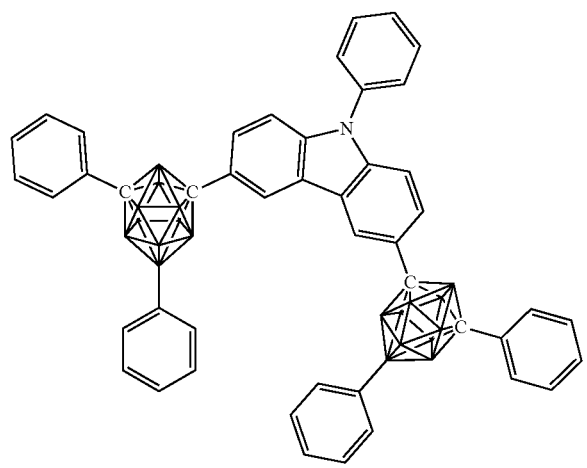
93
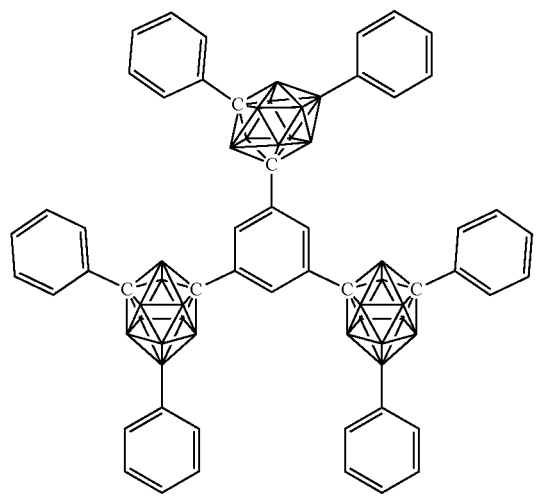
94
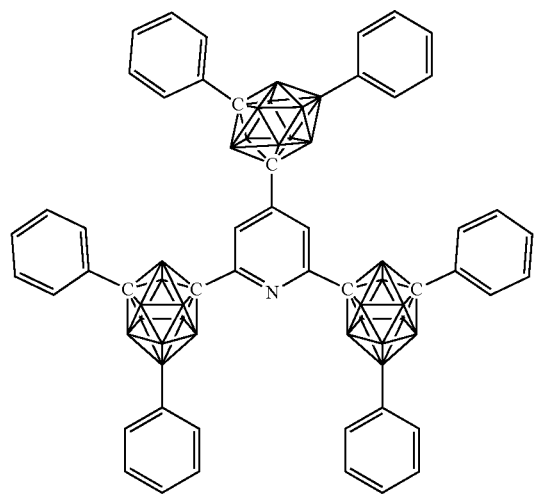
95
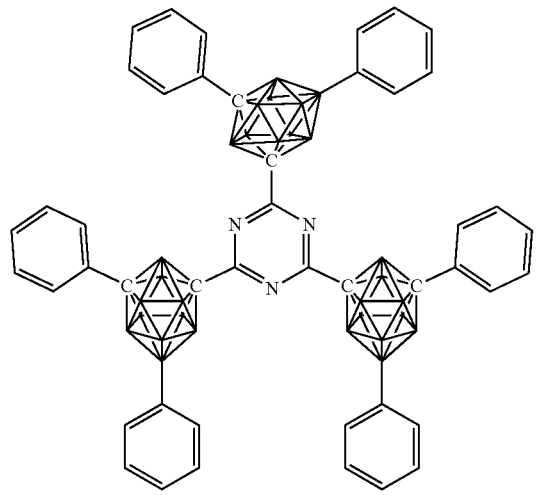
96
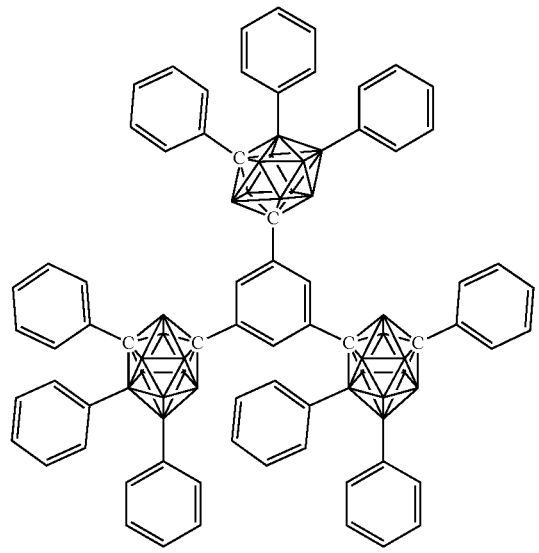
97

-continued
98
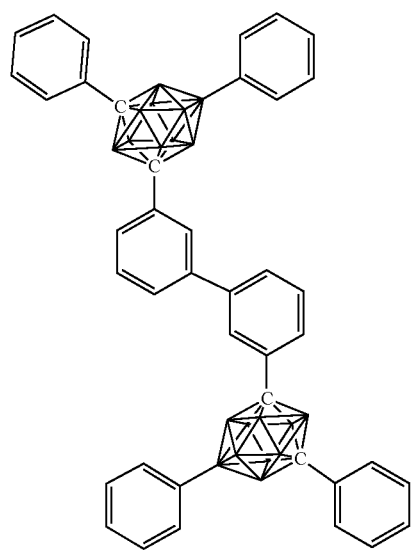
99
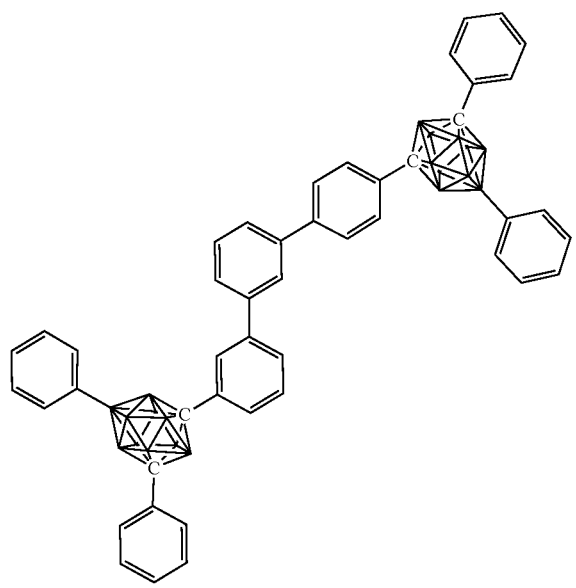
100
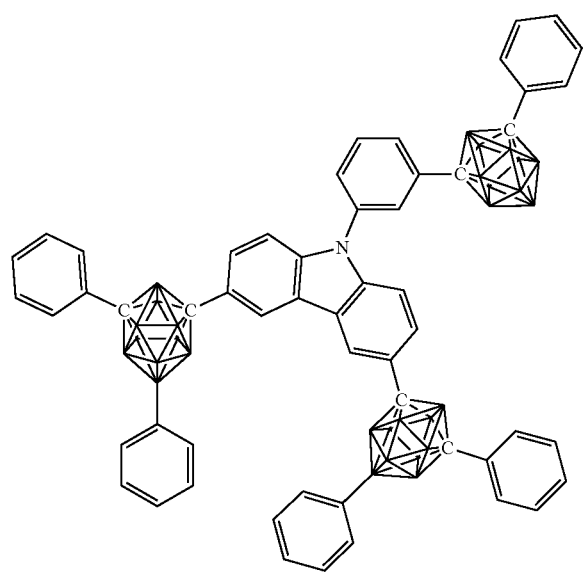
101
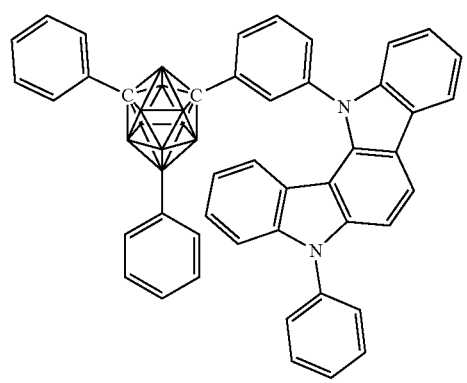

-continued
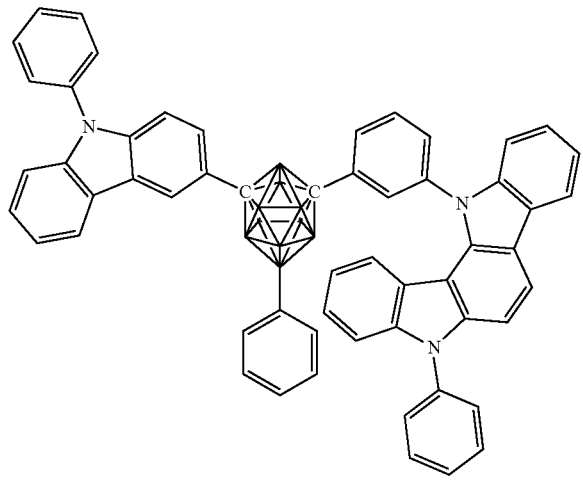
102
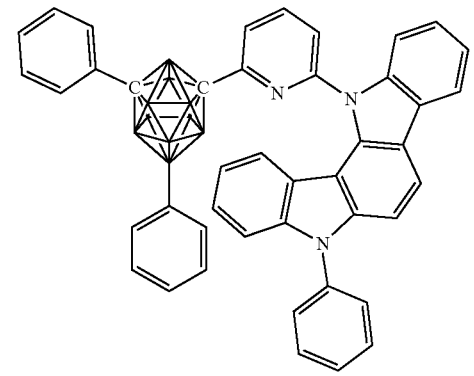
103
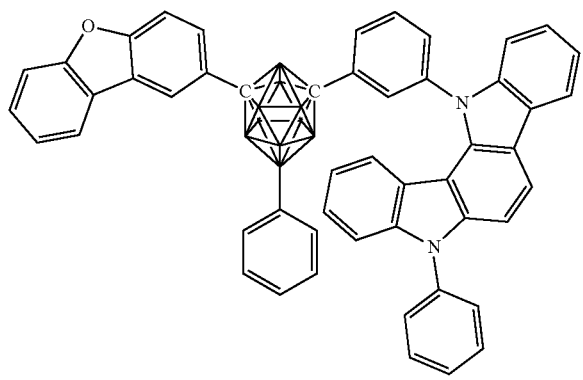
104
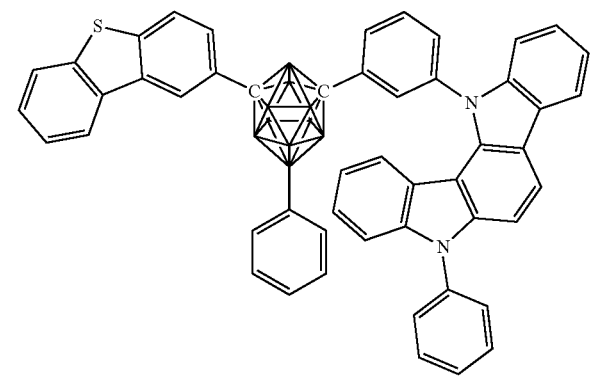
105
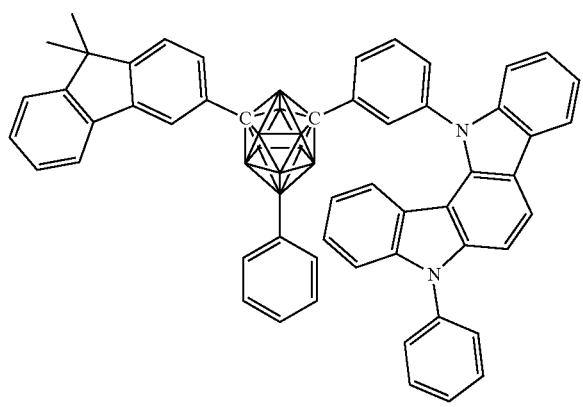
106
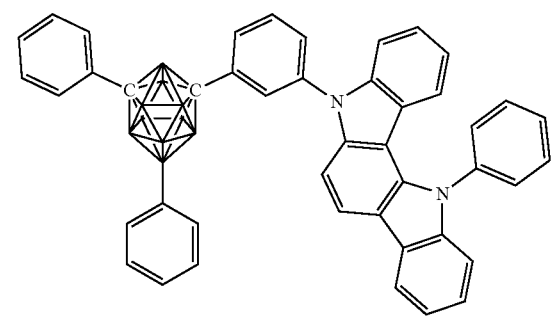
107

-continued

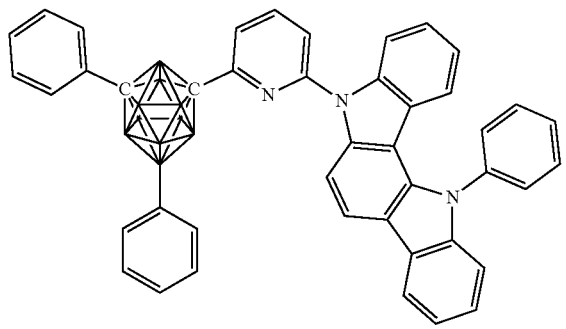
108

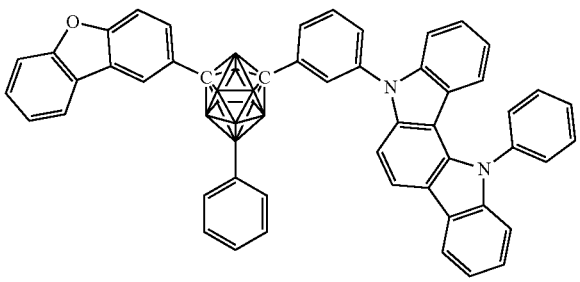
109

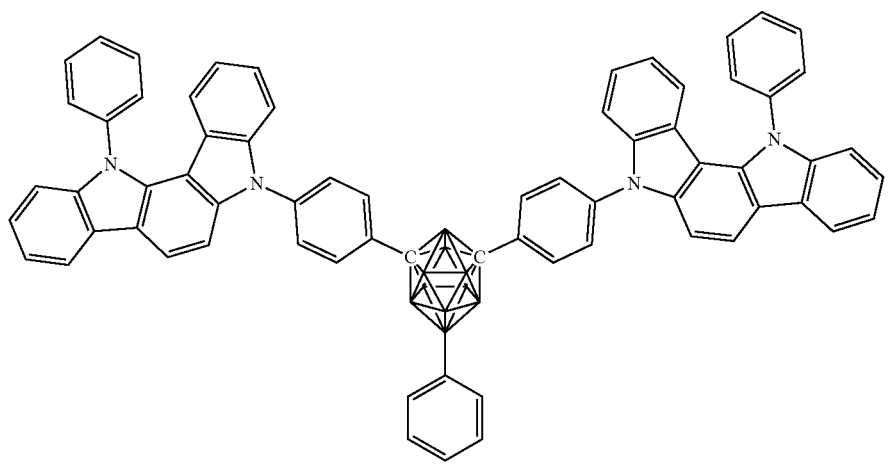
110

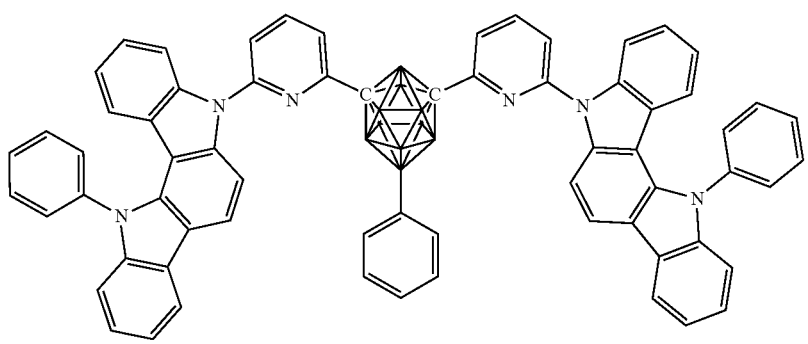
111

When the material for an organic electroluminescent device of the present invention (sometimes referred to as compound of the present invention, or compound or carborane compound represented by the general formula (1)) is contained in at least one of a plurality of organic layers of an organic EL device having a structure in which an anode, the plurality of organic layers, and a cathode are laminated on a substrate, an excellent organic electroluminescent device is provided. A light-emitting layer, an electron-transporting layer, or a hole-blocking layer is suitable as the organic layer in which the material is contained. Here, when the compound of the present invention is used in the light-emitting layer, the compound may be used as a host material for the light-emitting layer containing a fluorescent light-emitting, delayed fluorescent light-emitting, or phosphorescent light-emitting dopant. In addition, the compound of the present invention may be used as an organic light-emitting material that radiates fluorescence and delayed fluorescence. When the compound of the present invention is used as an organic light-emitting material that radiates fluorescence and delayed fluorescence, any other organic compound having a value for at least one of excited singlet energy or excited triplet energy higher than that of the compound of the present invention is preferably used as the host material. The compound of the present invention is particularly preferably incorporated as a host material for the light-emitting layer containing the phosphorescent light-emitting dopant.

Next, an organic EL device using the material for an organic electroluminescent device of the present invention is described.

The organic EL device of the present invention includes organic layers including at least one light-emitting layer between an anode and a cathode laminated on a substrate. In addition, at least one of the organic layers contains the material for an organic electroluminescent device of the present invention. The material for an organic electroluminescent device of the present invention is advantageously contained in the light-emitting layer together with a phosphorescent light-emitting dopant.

Next, the structure of the organic EL device of the present invention is described with reference to the drawings. However, the structure of the organic EL device of the present invention is by no means limited to one illustrated in the drawings.

FIG. 1 is a sectional view for illustrating an example of the structure of a general organic EL device to be used in the present invention. Reference numeral 1 represents a substrate, reference numeral 2 represents an anode, reference numeral 3 represents a hole-injecting layer, reference numeral 4 represents a hole-transporting layer, reference numeral 5 represents a light-emitting layer, reference numeral 6 represents an electron-transporting layer, and reference numeral 7 represents a cathode. The organic EL device of the present invention may include an exciton-blocking layer adjacent to the light-emitting layer, or may include an electron-blocking layer between the light-emitting layer and the hole-injecting layer. The exciton-blocking layer may be inserted on any of the anode side and the cathode side of the light-emitting layer, and may also be inserted simultaneously on both sides. The organic EL device of the present invention includes the substrate, the anode, the light-emitting layer, and the cathode as its essential layers. The organic EL device of the present invention preferably includes a hole-injecting/transporting layer and an electron-injecting/transporting layer in addition to the essential layers, and more preferably includes a hole-blocking layer between the light-emitting layer and the electron-injecting/transporting layer. The hole-injecting/transporting layer means any one or both of the hole-injecting layer and the hole-transporting layer, and the electron-injecting/transporting layer means any one or both of an electron-injecting layer and the electron-transporting layer.

It is possible to adopt a reverse structure as compared to FIG. 1, that is, the reverse structure being formed by laminating the layers on the substrate 1 in the order of the cathode 7, the electron-transporting layer 6, the light-emitting layer 5, the hole-transporting layer 4, and the anode 2. In this case as well, some layers may be added or eliminated as required.

—Substrate—

The organic EL device of the present invention is preferably supported by a substrate. The substrate is not particularly limited, and any substrate that has long been conventionally used for an organic EL device may be used. For example, a substrate made of glass, a transparent plastic, quartz, or the like may be used.

—Anode—

Preferably used as the anode in the organic EL device is an anode formed by using, as an electrode substance, any of a metal, an alloy, an electrically conductive compound, and a mixture thereof, all of which have a large work function (4 eV or more). Specific examples of such electrode substance include metals such as Au and conductive transparent materials, such as CuI, indium tin oxide (ITO), $SnO_2$, and ZnO. In addition, a material such as IDIXO ($In_2O_3$—ZnO), which can produce an amorphous, transparent conductive film, may be used. In order to produce the anode, it may be possible to form any of those electrode substances into a thin film by using a method such as vapor deposition or sputtering and form a pattern having a desired shape thereon by photolithography. Alternatively, in the case of not requiring high pattern accuracy (about 100 μm or more), a pattern may be formed via a mask having a desired shape when any of the above-mentioned electrode substances is subjected to vapor deposition or sputtering. Alternatively, when a coatable substance, such as an organic conductive compound, is used, a wet film-forming method, such as a printing method or a coating method, may be used. When luminescence is taken out from the anode, the transmittance of the anode is desirably controlled to more than 10%. In addition, the sheet resistance of the anode is preferably several hundred ohms per square (Ω/□) or less. Further, the thickness of the film is, depending on its material, selected from the range of generally from 10 nm to 1,000 nm, preferably from 10 nm to 200 nm.

—Cathode—

Meanwhile, used as the cathode is a cathode formed by using, as an electrode substance, any of a metal (referred to as electron-injecting metal), an alloy, an electrically conductive compound, and a mixture thereof, all of which have a small work function (4 eV or less). Specific examples of such electrode substance include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Of those, for example, a mixture of an electron-injecting metal and a second metal, which is a stable metal having a larger work function value than the former metal, such as a magnesium/silver mixture, a magnesium/aluminum mixture, a magnesium/indium mixture, an aluminum/aluminum oxide ($Al_2O_3$) mixture, or a lithium/aluminum mixture, or aluminum, is suitable from the viewpoints of an electron-injecting property and durability against oxidation or the like. The cathode may be produced by forming any of those electrode substances into a thin film by using a method such as vapor deposition or sputtering. In addition, the sheet resistance of the cathode is preferably several hundred Ω/□ or less, and the thickness of the film is selected from the range of generally from 10 nm to 5 μm, preferably from 50 nm to 200 nm. In order for luminescence produced to pass through, any one of the anode and cathode of the organic EL device is preferably transparent or semi-transparent, because the light emission luminance improves.

In addition, after the above-mentioned metal has been formed into a film having a thickness of from 1 nm to 20 nm as a cathode, the conductive transparent material mentioned in the description of the anode is formed into a film on the cathode, thereby being able to produce a transparent or semi-transparent cathode. Through the application of this, a device in which both the anode and cathode have transparency can be produced.

—Light-Emitting Layer—

The light-emitting layer is a layer that emits light after the production of an exciton by the recombination of a hole injected from the anode and an electron injected from the cathode, and the light-emitting layer contains an organic light-emitting material and a host material.

When the light-emitting layer is a fluorescent light-emitting layer, at least one kind of fluorescent light-emitting material may be used alone as the fluorescent light-emitting material. However, it is preferred that the fluorescent light-emitting material be used as a fluorescent light-emitting dopant and the host material be contained.

The carborane compound represented by the general formula (1) may be used as the fluorescent light-emitting material in the light-emitting layer. However, the fluorescent light-emitting material is known through, for example, many patent literatures, and hence may be selected therefrom. Examples thereof include a benzoxazole derivative, a benzothiazole derivative, a benzimidazole derivative, a styrylbenzene derivative, a polyphenyl derivative, a diphenylbutadiene derivative, a tetraphenylbutadiene derivative, a naphthalimide derivative, a coumarin derivative, a fused aromatic compound, a perinone derivative, an oxadiazole derivative, an oxazine derivative, an aldazine derivative, a pyrrolidine derivative, a cyclopentadiene derivative, a bisstyrylanthracene derivative, a quinacridone derivative, a pyrrolopyridine derivative, a thiadiazolopyridine derivative, a styrylamine derivative, a diketopyrrolopyrrole derivative, an aromatic dimethylidene compound, various metal complexes typified by a metal complex of an 8-quinolinol derivative, and a metal complex, rare earth complex, or transition metal complex of a pyrromethene derivative, polymer compounds, such as polythiophene, polyphenylene, and polyphenylene vinylene, and an organic silane derivative. Of those, for example, the following compound is preferred: a fused aromatic compound, a styryl compound, a diketopyrrolopyrrole compound, an oxazine compound, or a pyrromethene metal complex, transition metal complex, or lanthanoid complex. For example, the following compound is more preferred: naphthacene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthacene, hexacene, anthanthrene, naphtho[2,1-f]isoquinoline, α-naphthaphenanthridine, phenanthroxazole, quinolino[6,5-f]quinoline, or benzothiophanthrene. Those compounds may each have an alkyl group, an aryl group, an aromatic heterocyclic group, or a diarylamino group as a substituent.

The carborane compound represented by the general formula (1) may be used as a fluorescent host material in the light-emitting layer. However, the fluorescent host material is known through, for example, many patent literatures, and hence may be selected therefrom. For example, the following material may be used: a compound having a fused aryl ring, such as naphthalene, anthracene, phenanthrene, pyrene, chrysene, naphthacene, triphenylene, perylene, fluoranthene, fluorene, or indene, or a derivative thereof; an aromatic amine derivative, such as N,N'-dinaphthyl-N,N'-diphenyl-4,4'-diphenyl-1,1'-diamine; a metal chelated oxinoid compound typified by tris (8-quinolinato)aluminum (III); a bisstyryl derivative, such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative, such as a polyphenylene vinylene derivative, a poly-p-phenylene derivative, a polyfluorene derivative, a polyvinyl carbazole derivative, or a polythiophene derivative. However, the fluorescent host material is not particularly limited thereto.

When the fluorescent light-emitting material is used as a fluorescent light-emitting dopant and the host material is contained, the content of the fluorescent light-emitting dopant in the light-emitting layer desirably falls within the range of from 0.01 wt % to 20 wt %, preferably from 0.1 wt % to 10 wt %.

An organic EL device typically injects charges from both of its electrodes, i.e., its anode and cathode into a light-emitting substance to produce a light-emitting substance in an excited state, and causes the substance to emit light. In the case of a charge injection-type organic EL device, it is said that 25% of the produced excitons are excited to a singlet excited state and the remaining 75% of the excitons are excited to a triplet excited state. As disclosed in Advanced Materials 2009, 21, 4802-4806, it has been known that after a specific fluorescent light-emitting substance has undergone an energy transition to a triplet excited state as a result of intersystem crossing or the like, the substance is subjected to inverse intersystem crossing to a singlet excited state by triplet-triplet annihilation or the absorption of thermal energy to radiate fluorescence, thereby expressing thermally activated delayed fluorescence. The organic EL device of the present invention can also express delayed fluorescence. In this case, the light emission may include both fluorescent light emission and delayed fluorescent light emission. Light emission from the host material may be present in part of the light emission.

When the light-emitting layer is a delayed fluorescent light-emitting layer, at least one kind of delayed fluorescent light-emitting material may be used alone as a delayed fluorescent light-emitting material. However, it is preferred that the delayed fluorescent light-emitting material be used as a delayed fluorescent light-emitting dopant and the host material be contained.

The carborane compound represented by the general formula (1) may be used as the delayed fluorescent light-emitting material in the light-emitting layer. However, a material selected from known delayed fluorescent light-emitting materials may also be used. Examples thereof include a tin complex, an indolocarbazole derivative, a copper complex, and a carbazole derivative. Specific examples thereof include, but not limited to, compounds disclosed in the following non patent literatures and patent literature.

(1) Adv. Mater. 2009, 21, 4802-4806, (2) Appl. Phys. Lett. 98, 083302 (2011), (3) JP 2011-213643 A, and (4) J. Am. Chem. Soc. 2012, 134, 14706-14709.

Specific examples of the delayed fluorescent light-emitting material are shown below, but the delayed fluorescent light-emitting material is not limited to the following compounds.

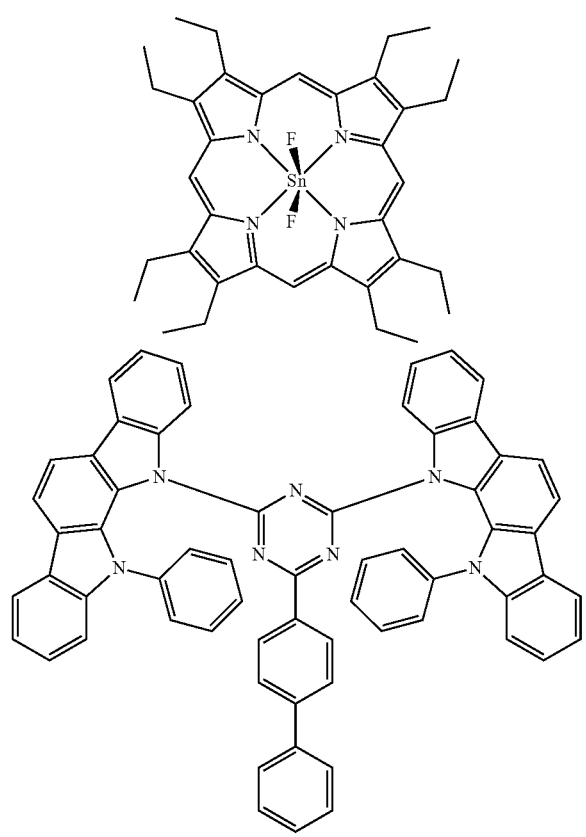

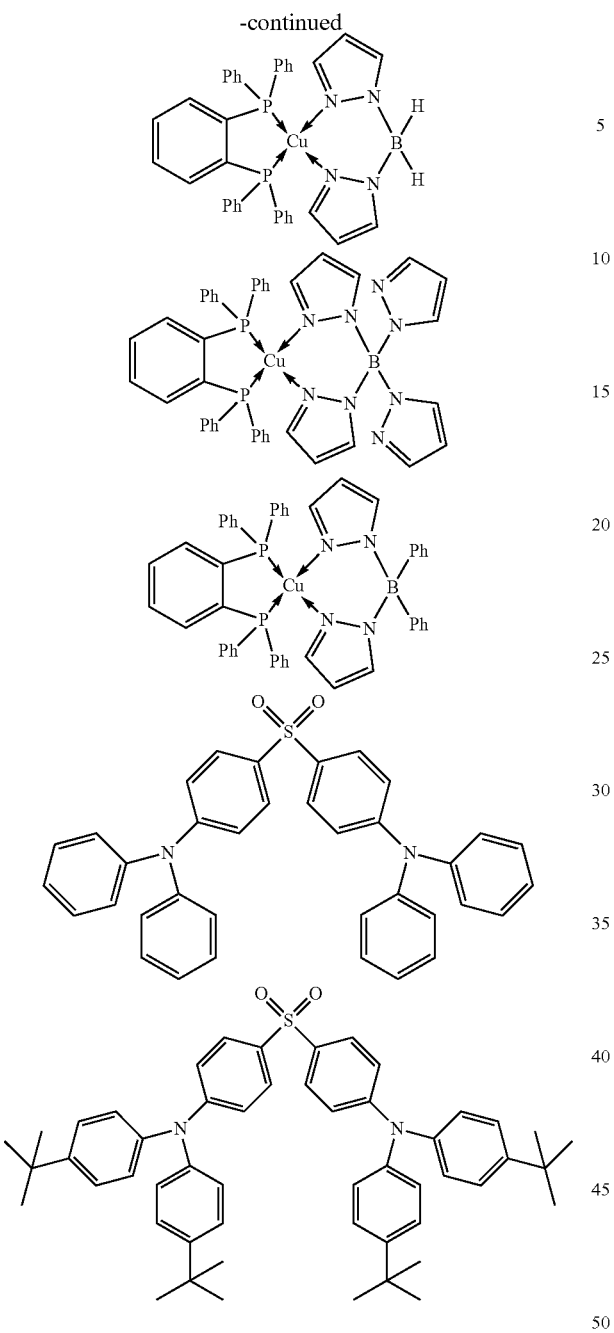

When the delayed fluorescent light-emitting material is used as a delayed fluorescent light-emitting dopant and the host material is contained, the content of the delayed fluorescent light-emitting dopant in the light-emitting layer desirably falls within the range of from 0.01 wt % to 50 wt %, preferably from 0.1 wt % to 20 wt %, more preferably from 0.01% to 10%.

The carborane compound represented by the general formula (1) may be used as the delayed fluorescent host material in the light-emitting layer. However, the delayed fluorescent host material may also be selected from compounds except the carborane compound. For example, the following compound may be used: a compound having a fused aryl ring, such as naphthalene, anthracene, phenanthrene, pyrene, chrysene, naphthacene, triphenylene, perylene, fluoranthene, fluorene, or indene, or a derivative thereof; an aromatic amine derivative, such as N,N'-dinaphthyl-N,N'-diphenyl-4,4'-diphenyl-, 1'-diamine; a metal chelated oxinoid compound typified by tris(8-quinolinato)aluminum(III); a bisstyryl derivative, such as a distyrylbenzene derivative; a tetraphenylbutadiene derivative; an indene derivative; a coumarin derivative; an oxadiazole derivative; a pyrrolopyridine derivative; a perinone derivative; a cyclopentadiene derivative; a pyrrolopyrrole derivative; a thiadiazolopyridine derivative; a dibenzofuran derivative; a carbazole derivative; an indolocarbazole derivative; a triazine derivative; or a polymer-based derivative, such as a polyphenylene vinylene derivative, a poly-p-phenylene derivative, a polyfluorene derivative, a polyvinyl carbazole derivative, a polythiophene derivative, or an arylsilane derivative. However, the delayed fluorescent host material is not particularly limited thereto.

When the light-emitting layer is a phosphorescent light-emitting layer, the light-emitting layer contains a phosphorescent light-emitting dopant and a host material. It is recommended to use, as a material for the phosphorescent light-emitting dopant, a material containing an organic metal complex including at least one metal selected from ruthenium, rhodium, palladium, silver, rhenium, osmium, iridium, platinum, and gold.

Preferred examples of the phosphorescent light-emitting dopant include complexes such as Ir(ppy)$_3$, complexes such as Ir(bt)$_2$.acac$_3$, and complexes such as PtOEt$_3$, the complexes each having a noble metal element, such as Ir, as a central metal. Specific examples of those complexes are shown below, but the complexes are not limited to the following compounds.

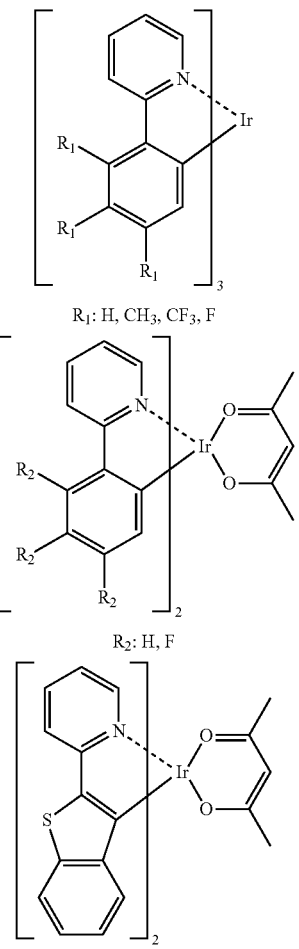

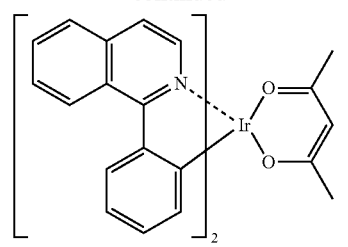
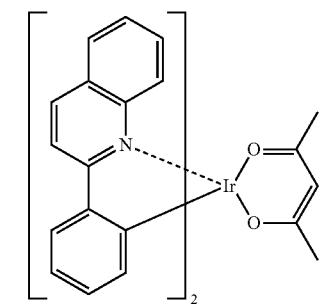
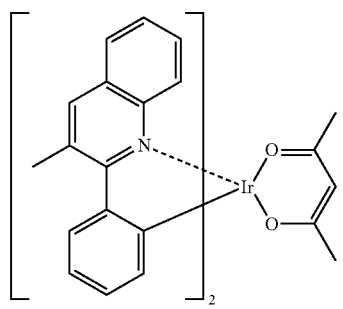
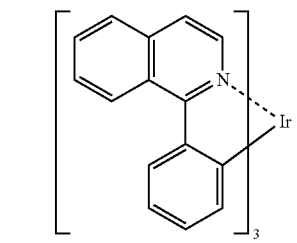
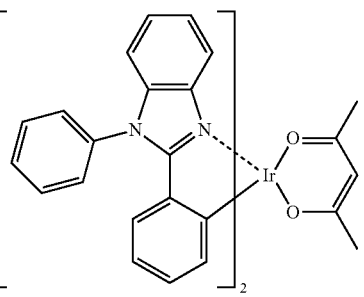
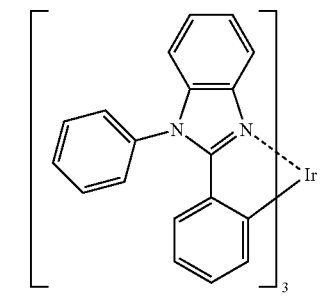
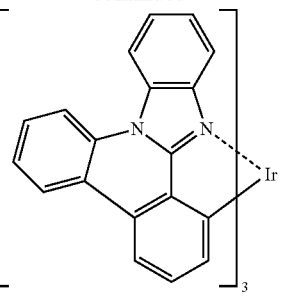
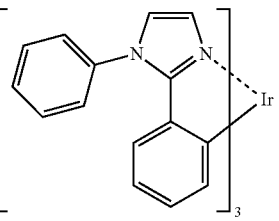
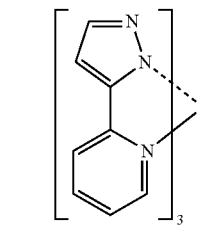
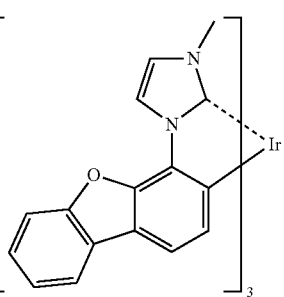
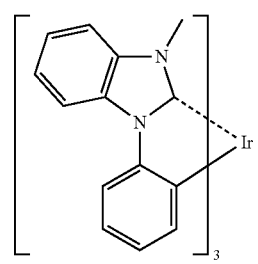
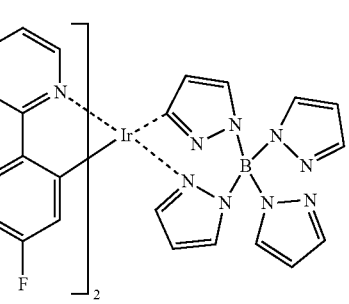

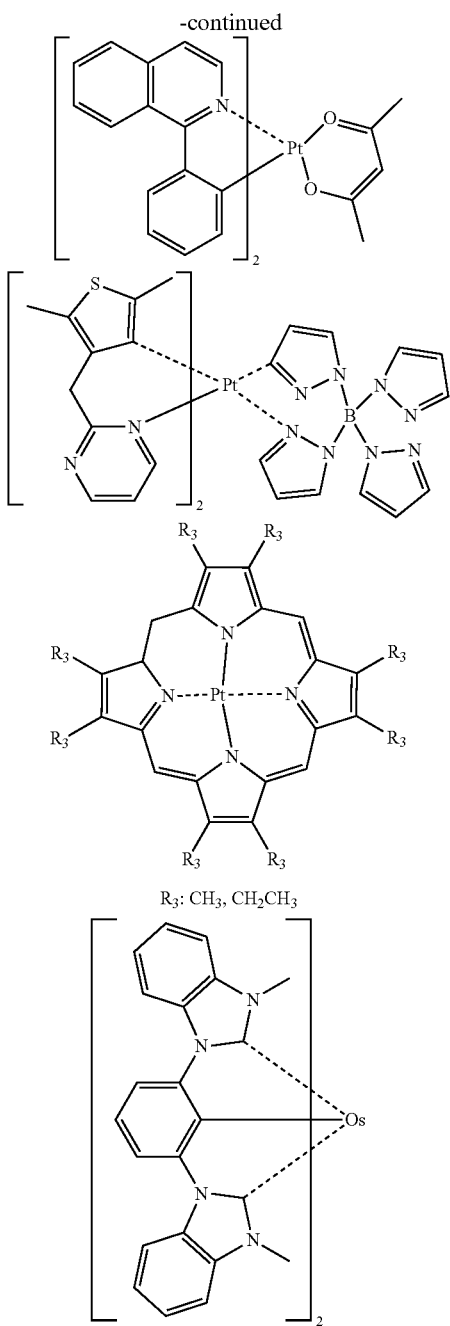

R₃: CH₃, CH₂CH₃

It is desired that the content of the phosphorescent light-emitting dopant in the light-emitting layer fall within the range of from 2 wt % to 40 wt %, preferably from 5 wt % to 30 wt %.

When the light-emitting layer is a phosphorescent light-emitting layer, it is preferred to use, as a host material in the light-emitting layer, the carborane compound of the present invention. However, when the carborane compound is used in any other organic layer except the light-emitting layer, the material to be used in the light-emitting layer may be any other host material except the carborane compound. In addition, the carborane compound may be used in combination with any other host material. Further, a plurality of kinds of known host materials may be used in combination.

It is preferred to use, as a known host compound that may be used, a compound that has a hole-transporting ability or an electron-transporting ability, is capable of preventing luminescence from having a longer wavelength, and has a high glass transition temperature.

Any such other host material is known through, for example, many patent literatures, and hence may be selected therefrom. Specific examples of the host material include, but not particularly limited to an indole derivative, a carbazole derivative, an indolocarbazole derivative, a triazole derivative, an oxazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, a styrylanthracene derivative, a fluorenone derivative, a hydrazone derivative, a stilbene derivative, a silazane derivative, an aromatic tertiary amine compound, a styrylamine compound, an aromatic dimethylidene-based compound, a porphyrin-based compound, an anthraquinodimethane derivative, an anthrone derivative, a diphenylquinone derivative, a thiopyran dioxide derivative, a heterocyclic tetracarboxylic acid anhydride, such as naphthalene perylene, various metal complexes typified by metal complexes of a phthalocyanine derivative and an 8-quinolinol derivative, and metal complexes of metal phthalocyanine, benzoxazole, and benzothiazole derivatives, and polymer compounds, such as a polysilane-based compound, a poly(N-vinylcarbazole) derivative, an aniline-based copolymer, a thiophene oligomer, a polythiophene derivative, a polyphenylene derivative, a polyphenylenevinylene derivative, and a polyfluorene derivative.

The light-emitting layer, which may be any one of a fluorescent light-emitting layer, a delayed fluorescent light-emitting layer, and a phosphorescent light-emitting layer, is preferably the phosphorescent light-emitting layer.

—Injecting Layer—

The injecting layer refers to a layer formed between an electrode and an organic layer for the purposes of lowering a driving voltage and improving light emission luminance, and includes a hole-injecting layer and an electron-injecting layer. The injecting layer may be interposed between the anode and the light-emitting layer or the hole-transporting layer, or may be interposed between the cathode and the light-emitting layer or the electron-transporting layer. The injecting layer may be formed as required.

—Hole-Blocking Layer—

The hole-blocking layer has, in a broad sense, the function of an electron-transporting layer, and is formed of a hole-blocking material that has a remarkably small ability to transport holes while having a function of transporting electrons, and hence the hole-blocking layer is capable of improving the probability of recombining an electron and a hole by blocking holes while transporting electrons.

It is preferred to use the carborane compound of the present invention for the hole-blocking layer. However, when the carborane compound is used in any other organic layer, a known material for a hole-blocking layer may be used. In addition, a material for the electron-transporting layer to be described later may be used as a material for the hole-blocking layer as required.

—Electron-Blocking Layer—

The electron-blocking layer is formed of a material that has a remarkably small ability to transport electrons while having a function of transporting holes, and hence the electron-blocking layer is capable of improving the probability of recombining an electron and a hole by blocking electrons while transporting holes.

A material for the hole-transporting layer to be described later may be used as a material for the electron-blocking layer as required. The thickness of the electron-blocking layer is preferably from 3 nm to 100 nm, more preferably from 5 nm to 30 nm.

—Exciton-Blocking Layer—

The exciton-blocking layer refers to a layer for blocking excitons produced by the recombination of a hole and an electron in the light-emitting layer from diffusing into charge-transporting layers. The insertion of this layer enables efficient confinement of the excitons in the light-emitting layer, thereby being able to improve the luminous efficiency of the device. The exciton blocking layer may be inserted on any of the anode side and the cathode side of the adjacent light-emitting layer, and may also be inserted simultaneously on both sides.

The carborane compound represented by the general formula (1) may be used as a material for the exciton-blocking layer. However, as other materials therefor, there are given, for example, 1,3-dicarbazolylbenzene (mCP) and bis(2-methyl-8-quinolinolato)-4-phenylphenolatoaluminum (III) (BAlq).

—Hole-Transporting Layer—

The hole-transporting layer is formed of a hole-transporting material having a function of transporting holes, and a single hole-transporting layer or a plurality of hole-transporting layers may be formed.

The hole-transporting material has a hole-injecting property or a hole-transporting property or has an electron-blocking property, and any of an organic material and an inorganic material may be used as the hole-transporting material. It is preferred to use the carborane compound represented by the general formula (1) as a known hole-transporting material that may be used. However, any compound selected from conventionally known compounds may be used. Examples of the known hole-transporting material that may be used include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer, and a conductive high-molecular oligomer, in particular, a thiophene oligomer. Of those, a porphyrin compound, an aromatic tertiaryamine compound, or a styrylamine compound is preferably used, and an aromatic tertiary amine compound is more preferably used.

—Electron-Transporting Layer—

The electron-transporting layer is formed of a material having a function of transporting electrons, and a single electron-transporting layer or a plurality of electron-transporting layers may be formed.

An electron-transporting material (which also serves as a hole-blocking material in some cases) only needs to have a function of transferring electrons injected from the cathode into the light-emitting layer. It is preferred to use the carborane compound of the present invention for the electron-transporting layer. However, any compound selected from conventionally known compounds may be used. Examples thereof include a nitro-substituted fluorene derivative, a diphenylquinone derivative, a thiopyran dioxide derivative, a carbodiimide, a fluorenylidenemethane derivative, anthraquinodimethane and anthrone derivatives, and an oxadiazole derivative. Further, a thiadiazole derivative prepared by substituting an oxygen atom on an oxadiazole ring with a sulfur atom in the oxadiazole derivative or a quinoxaline derivative that has a quinoxaline ring known as an electron withdrawing group may be used as the electron-transporting material. Further, a polymer material in which any such material is introduced in a polymer chain or is used as a polymer main chain may be used.

EXAMPLES

Now, the present invention is described in more detail by way of Examples. It should be appreciated that the present invention is not limited to Examples below and may be carried out in various forms as long as the various forms do not deviate from the gist of the present invention.

A carborane compound serving as a material for an organic electroluminescent device was synthesized according to the following route. The number of each compound corresponds to the number given to the chemical formula.

Example 1 (Synthesis Example)

A compound 9 was synthesized in accordance with the following reaction formulae.

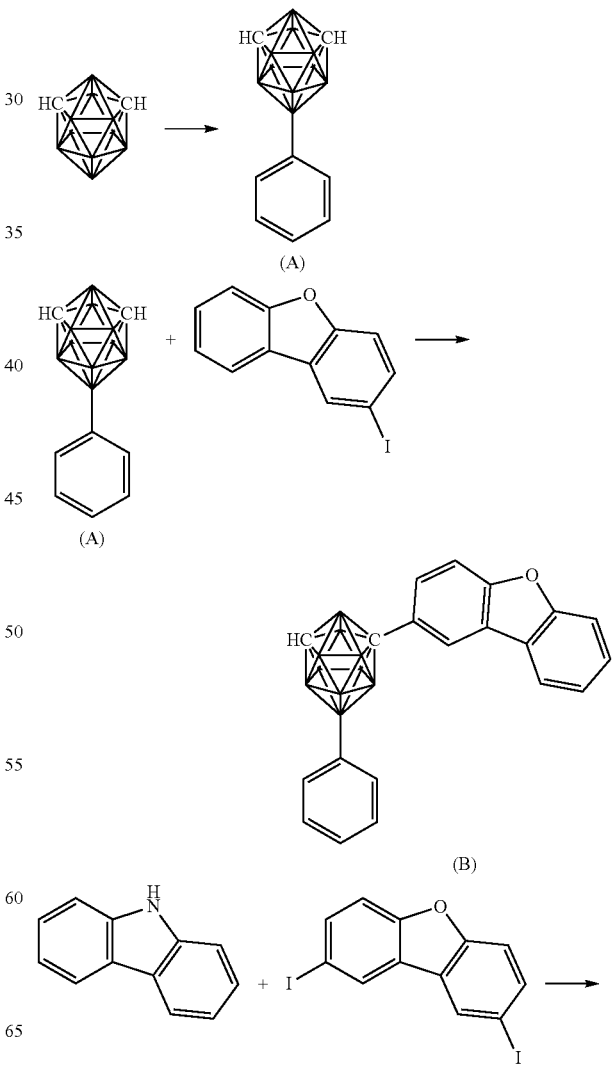

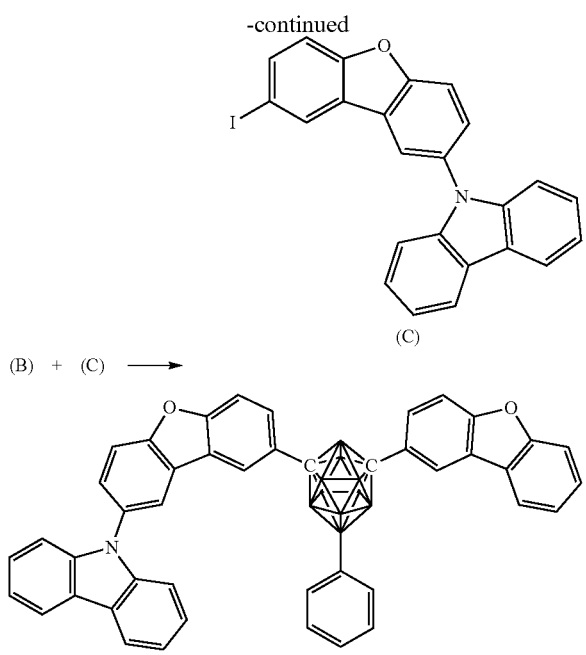

(C)

(B) + (C) →

Under a nitrogen atmosphere, 41.6 g (0.28 mol) of m-carborane, 92.4 g (0.56 mol) of iodine monochloride, 4.0 g (0.03 mol) of aluminum chloride, and 1 L of methylene chloride were loaded, and were stirred at room temperature for 6 hr. After that, the precipitated crystal was taken by filtration and recrystallized with methylene chloride to provide 57.6 g (0.26 mol, yield: 93%) of an intermediate A.

Under a nitrogen atmosphere, 53.5 g (0.243 mol) of the intermediate A and 350 mL of 1,2-dimethoxyethane (DME) were loaded, and the resultant DME solution was cooled to 0° C. 96.8 mL of a 2.69 M solution of n-butyllithium in hexane was dropped to the solution, and the mixture was stirred under ice cooling for 30 min. 67 mL of pyridine was added to the resultant, and the mixture was stirred at room temperature for 10 min. After that, 75.6 g (0.763 mol) of copper (I) chloride was added to the resultant, and the mixture was stirred at 65° C. for 30 min. After that, 76.4 g (0.260 mol) of 2-iododibenzofuran was added to the resultant, and the mixture was stirred at 95° C. overnight. The reaction solution was cooled to room temperature. After that, the precipitated crystal was separated by filtration, and the solvent was distilled off under reduced pressure. The resultant residue was purified by silica gel column chromatography to provide 37.6 g (97.2 mmol, yield: 40%) of an intermediate B.

Under a nitrogen atmosphere, 30.0 g (0.07 mol) of 2,8-diiododibenzofuran, 11.9 g (0.07 mol) of carbazole, 1.33 g (7.0 mmol) of copper iodide, 44.6 g (0.21 mol) of tripotassium phosphate, 2.4 g (21.0 mmol) of trans-1,2-cyclohexanediamine, and 1 L of 1,4-dioxane were loaded, and were stirred at 115° C. overnight. After the reaction solution had been cooled to room temperature, the precipitated crystal was taken by filtration, and the solvent was distilled off under reduced pressure. The resultant residue was purified by silica gel column chromatography to provide 15.8 g (3.43 mmol, yield: 49%) of an intermediate C as a white solid.

Under a nitrogen atmosphere, 11.0 g (0.0285 mol) of the intermediate B and 63.0 mL of 1,2-dimethoxyethane (DME) were loaded, and the resultant DME solution was cooled to 0° C. 11.3 mL of a 2.69 M solution of n-butyllithium in hexane was dropped to the solution, and the mixture was stirred under ice cooling for 30 min. 7.8 mL of pyridine was added to the mixture, and the whole was stirred at room temperature for 10 min. After that, 8.7 g (88.4 mmol) of copper(I) chloride was added to the resultant, and the mixture was stirred at 65° C. for 30 min. After that, 14.0 g (0.0305 mol) of the intermediate C was added to the mixture, and the whole was stirred at 95° C. for 4 d. After the reaction solution had been cooled to room temperature, the precipitated crystal was taken by filtration, and the solvent was distilled off under reduced pressure. The resultant residue was purified by silica gel column chromatography to provide 4.09 g (5.70 mmol, yield: 20) of the compound 9 (APCI-TOFMS, m/z 720 [M+H]$^+$).

Example 2 (Synthesis Example)

A compound 103 was synthesized in accordance with the following reaction formulae.

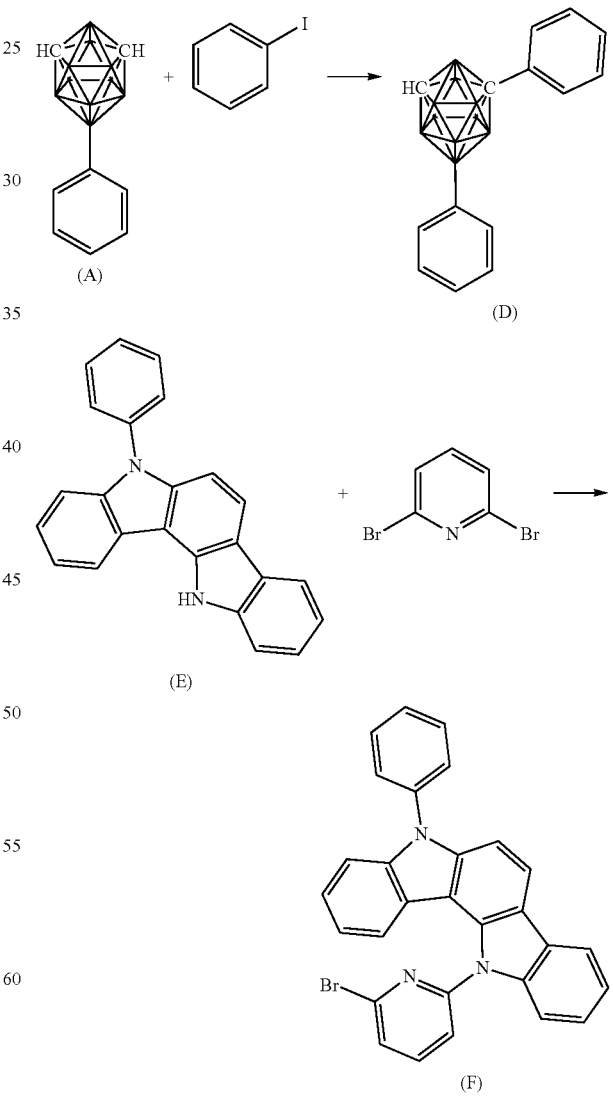

(D) + (F) →

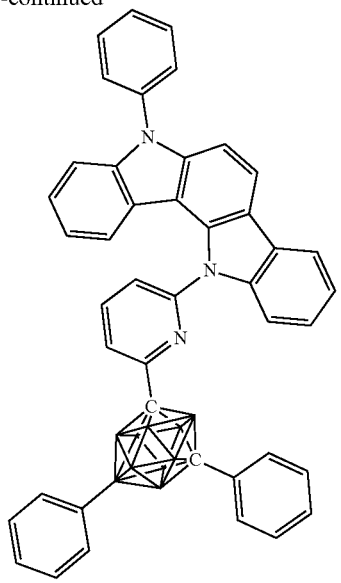

Under a nitrogen atmosphere, 53.5 g (0.243 mol) of the intermediate A and 340 mL of 1,2-dimethoxyethane (DME) were loaded, and the resultant DME solution was cooled to 0° C. 96.6 mL of a 2.69 M solution of n-butyllithium in hexane was dropped to the solution, and the mixture was stirred under ice cooling for 30 min. 70 mL of pyridine was added to the resultant, and the mixture was stirred at room temperature for 10 min. After that, 74.6 g (0.753 mol) of copper (I) chloride was added to the resultant, and the mixture was stirred at 65° C. for 30 min. After that, 53.0 g (0.260 mol) of iodobenzene was added to the resultant, and the mixture was stirred at 95° C. overnight. After the reaction solution had been cooled to room temperature, the precipitated crystal was taken by filtration, and the solvent was distilled off under reduced pressure. The resultant residue was purified by silica gel column chromatography to provide 57.7 g (0.195 mol, yield: 80.1%) of an intermediate D.

Under a nitrogen atmosphere, 50.0 g (0.15 mol) of an intermediate E, 142.6 g (0.60 mol) of 2,6-dibromopyridine, 5.60 g (0.028 mol) of copper iodide, 160 g (0.760 mol) of tripotassium phosphate, 34.0 g (0.30 mol) of trans-1,2-cyclohexanediamine, and 1.5 L of 1,4-dioxane were loaded, and were stirred at 120° C. overnight. After the reaction solution had been cooled to room temperature, the precipitated crystal was taken by filtration, and the solvent was distilled off under reduced pressure. The resultant residue was purified by silica gel column chromatography to provide 42.8 g (87.6 mmol, yield: 58.4%) of an intermediate F as a white solid.

Under a nitrogen atmosphere, 11.4 g (0.0383 mol) of the intermediate D and 85 mL of DME were loaded, and the resultant DME solution was cooled to 0° C. 15.0 mL of a 2.65 M solution of n-butyllithium in hexane was dropped to the solution, and the mixture was stirred under ice cooling for 30 min. 10.5 mL of pyridine was added to the resultant, and the mixture was stirred at room temperature for 10 min. After that, 11.8 g (0.118 mol) of copper(I) chloride was added to the resultant, and the mixture was stirred at 65° C. for 30 min. After that, 20 g (0.041 mol) of the intermediate F was added to the resultant, and the mixture was stirred at 95° C. for 2 d. The reaction solution was cooled to room temperature. After that, the precipitated crystal was separated by filtration, and the solvent was distilled off under reduced pressure. The resultant residue was purified by silica gel column chromatography to provide 5.2 g (7.35 mmol, yield: 19.2%) of the compound 103 (APCI-TOFMS, m/z 706 [M+H]$^+$).

Compounds 1, 7, 26, 56, 57, 94 and 110 were synthesized in conformity with the synthesis examples. In addition, compounds H-1 and H-2 for comparison were synthesized.

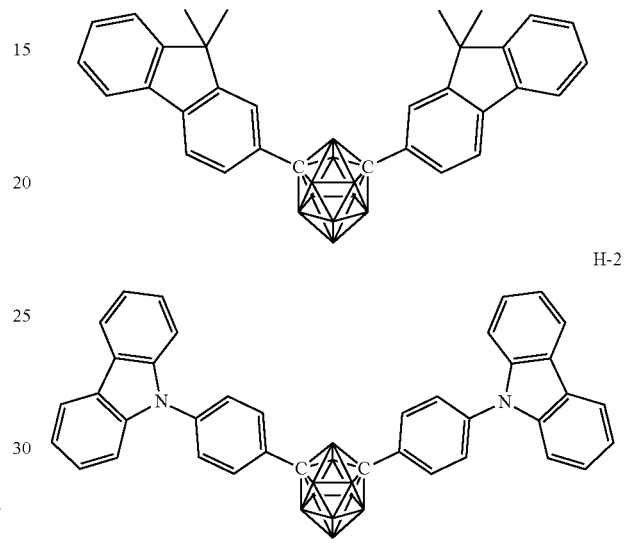

Each thin film was laminated by a vacuum deposition method at a degree of vacuum of 2.0×10$^{-5}$ Pa on a glass substrate on which an anode formed of indium tin oxide (ITO) having a thickness of 70 nm had been formed. First, copper phthalocyanine (CuPC) was formed into a layer having a thickness of 30 nm to serve as a hole-injecting layer on the ITO. Next, diphenyl naphthyl diamine (NPD) was formed into a layer having a thickness of 15 nm to serve as a hole-transporting layer. Next, the compound 1 serving as a host material for a light-emitting layer and an iridium complex [iridium(III) bis(4,6-di-fluorophenyl)-pyridinato-N,C2'lpicolinate] (FIrpic) serving as a blue phosphorescent material as a dopant were co-deposited from different deposition sources onto the hole-transporting layer to form a light-emitting layer having a thickness of 30 nm. The concentration of FIrpic was 20%. Next, Alq$_3$ was formed into a layer having a thickness of 25 nm to serve as an electron-transporting layer. Further, lithium fluoride (LiF) was formed into a layer having a thickness of 1.0 nm to serve as an electron-injecting layer on the electron-transporting layer. Finally, aluminum (Al) was formed into a layer having a thickness of 70 nm to serve as an electrode on the electron-injecting layer. The resultant organic EL device has such a layer construction that the electron-injecting layer is added between the cathode and the electron-transporting layer in the organic EL device illustrated in FIG. 1.

An external power source was connected to the resultant organic EL device to apply a DC voltage to the device. As a result, it was confirmed that the device had such light-emitting characteristics as shown in Table 1. The columns "luminance", "voltage", and "luminous efficiency" in Table 1 show values at 2.5 mA/cm$^2$ (initial characteristics). The maximum wavelength of the emission spectrum of the device was 475 nm, and hence the acquisition of light emission from FIrpic was found.

Examples 4 to 11

Organic EL devices were each produced in the same manner as in Example 3 except that the compound 7, 9, 26, 56, 57, 94, 103, or 110 was used instead of the compound 1 as the host material for the light-emitting layer in Example 3.

Comparative Example 1

An organic EL device was produced in the same manner as in Example 3 except that mCP was used as the host material for the light-emitting layer in Example 3.

Comparative Examples 2 and 3

Organic EL devices were each produced in the same manner as in Example 3 except that the compound H-1 or H-2 was used as the host material for the light-emitting layer in Example 3.

The organic EL devices obtained in Examples 4 to 11 and Comparative Examples 1 to 3 were evaluated in the same manner as in Example 3. As a result, it was confirmed that the devices had such light-emitting characteristics as shown in Table 1. The maximum wavelength of each of the emission spectra of the organic EL devices was 475 nm, and hence the acquisition of light emission from FIrpic was identified.

TABLE 1

| | Host material compound | Luminance (cd/m$^2$) | Voltage (V) | Visual luminous efficiency (lm/W) |
|---|---|---|---|---|
| Example 3 | 1 | 170 | 7.3 | 2.9 |
| Example 4 | 7 | 170 | 8.1 | 2.6 |
| Example 5 | 9 | 170 | 6.7 | 3.2 |
| Example 6 | 26 | 180 | 8.1 | 2.8 |
| Example 7 | 56 | 170 | 6.7 | 3.2 |
| Example 8 | 57 | 160 | 6.7 | 3.0 |
| Example 9 | 94 | 170 | 5.9 | 3.6 |
| Example 10 | 103 | 160 | 6.9 | 2.9 |
| Example 11 | 110 | 160 | 7.3 | 2.7 |
| Comparative Example 1 | mCP | 140 | 8.7 | 2.0 |
| Comparative Example 2 | H-1 | 100 | 7.7 | 1.6 |
| Comparative Example 3 | H-2 | 140 | 7.5 | 2.3 |

As can be seen from Table 1, Examples 3 to 11 each using the carborane compound of the present invention in the light-emitting layer each show luminous efficiency more satisfactory than that of each of Comparative Examples 1 to 3.

Example 12

Each thin film was laminated by a vacuum deposition method at a degree of vacuum of $2.0 \times 10^{-5}$ Pa on a glass substrate on which an anode formed of indium tin oxide (ITO) having a thickness of 70 nm had been formed. First, copper phthalocyanine (CuPC) was formed into a layer having a thickness of 30 nm to serve as a hole-injecting layer on the ITO. Next, diphenylnaphthyldiamine (NPD) was formed into a layer having a thickness of 15 nm to serve as a hole-transporting layer. Next, the compound 1 serving as a host material for a light-emitting layer and Ir(ppy)$_3$ serving as a dopant were co-deposited from different deposition sources onto the hole-transporting layer to form a light-emitting layer having a thickness of 30 nm. The concentration of Ir(ppy)$_3$ was 10%. Next, Alq$_3$ was formed into a layer having a thickness of 25 nm to serve as an electron-transporting layer. Further, lithium fluoride (LiF) was formed into a layer having a thickness of 1 nm to serve as an electron-injecting layer on the electron-transporting layer. Finally, aluminum (Al) was formed into a layer having a thickness of 70 nm to serve as an electrode on the electron-injecting layer. Thus, an organic EL device was produced.

An external power source was connected to the resultant organic EL device to apply a DC voltage to the device. As a result, it was confirmed that the device had such light-emitting characteristics as shown in Table 2. The columns "luminance", "voltage", and "luminous efficiency" in Table 2 show values at the time of driving at 20 mA/cm$^2$ (initial characteristics). The maximum wavelength of the emission spectrum of the device was 530 nm, and hence the acquisition of light emission from Ir(ppy)$_3$ was found.

Examples 13 to 20

Organic EL devices were each produced in the same manner as in Example 12 except that the compound 7, 9, 26, 56, 57, 94, 103, or 110 was used as a host material for the light-emitting layer in Example 13 instead of the compound 1.

Comparative Examples 4 to 6

Organic EL devices were each produced in the same manner as in Example 8 except that CBP, H-1, or H-2 was used as a host material for the light-emitting layer in Example 12.

The organic EL devices obtained in Examples and Comparative Examples above were evaluated in the same manner as in Example 12. As a result, it was confirmed that the devices had such light-emitting characteristics as shown in Table 2. The maximum wavelength of each of the emission spectra of the organic EL devices obtained in Examples and Comparative Examples above was 530 nm, and hence the acquisition of light emission from Ir(ppy)$_3$ was identified.

TABLE 2

| | Host material compound | Luminance (cd/m$^2$) | Voltage (V) | Visual luminous efficiency (lm/W) |
|---|---|---|---|---|
| Example 12 | 1 | 2,200 | 8.8 | 3.9 |
| Example 13 | 7 | 1,800 | 9.8 | 2.9 |
| Example 14 | 9 | 2,100 | 8.1 | 4.1 |
| Example 15 | 26 | 2,200 | 9.8 | 3.5 |
| Example 16 | 56 | 2,100 | 8.1 | 4.1 |
| Example 17 | 57 | 2,100 | 8.1 | 4.1 |
| Example 18 | 94 | 1,700 | 7.1 | 3.8 |
| Example 19 | 103 | 2,000 | 8.4 | 3.8 |
| Example 20 | 110 | 2,000 | 8.9 | 3.5 |
| Comparative Example 4 | CBP | 1,100 | 8.7 | 2.0 |
| Comparative Example 5 | H-1 | 1,200 | 8.5 | 2.2 |
| Comparative Example 6 | H-2 | 1,000 | 8.3 | 1.9 |

As can be seen from Table 2, Examples 12 to 20 each using the carborane compound of the present invention in the light-emitting layer each show luminous efficiency more satisfactory than that of each of Comparative Examples 4 to 6.

Example 21

Each thin film was laminated by a vacuum deposition method at a degree of vacuum of $2.0 \times 10^{-5}$ Pa on a glass substrate on which an anode formed of indium tin oxide (ITO) having a thickness of 70 nm had been formed. First, copper phthalocyanine (CuPC) was formed into a layer having a thickness of 30 nm to serve as a hole-injecting layer on the ITO. Next, diphenylnaphthyldiamine (NPD) was formed into a layer having a thickness of 15 nm to serve as a hole-transporting layer. Next, mCP serving as a host material for a light-emitting layer and FIrpic serving as a dopant were co-deposited from different deposition sources onto the hole-transporting layer to form a light-emitting layer having a thickness of 30 nm. The concentration of FIrpic was 20%. Next, the compound 1 was formed into a layer having a thickness of 5 nm to serve as a hole-blocking layer on the light-emitting layer. Next, $Alq_3$ was formed into a layer having a thickness of 20 nm to serve as an electron-transporting layer. Further, lithium fluoride (LiF) was formed into a layer having a thickness of 1.0 nm to serve as an electron-injecting layer on the electron-transporting layer. Finally, aluminum (Al) was formed into a layer having a thickness of 70 nm to serve as an electrode on the electron-injecting layer. The resultant organic EL device has such a layer construction that in the organic EL device illustrated in FIG. 1, the electron-injecting layer is added between the cathode and the electron-transporting layer, and the hole-blocking layer is added between the light-emitting layer and the electron-transporting layer.

An external power source was connected to the resultant organic EL device to apply a DC voltage to the device. As a result, it was confirmed that the device had such light-emitting characteristics as shown in Table 3. The columns "luminance", "voltage", and "luminous efficiency" in Table 3 show values at the time of driving at 20 $mA/cm^2$ (initial characteristics). The maximum wavelength of the emission spectrum of the device was 475 nm, and hence the acquisition of light emission from FIrpic was found.

Examples 22 to 27

Organic EL devices were each produced in the same manner as in Example 21 except that the compound 7, 9, 26, 56, 57, or 94 was used as a hole-blocking material in Example 21 instead of the compound 1.

Comparative Example 7

An organic EL device was produced in the same manner as in Example 21 except that: the thickness of $Alq_3$ serving as the electron-transporting layer in Example 21 was changed to 25 nm; and the hole-blocking layer was not formed.

Comparative Examples 8 and 9

Organic EL devices were each produced in the same manner as in Example 21 except that the compound H-1 or H-2 was used as a hole-blocking material in Example 21.

The organic EL devices obtained in Examples and Comparative Examples above were evaluated in the same manner as in Example 21. As a result, it was confirmed that the devices had such light-emitting characteristics as shown in Table 3. The maximum wavelength of each of the emission spectra of the organic EL devices obtained in Examples and Comparative Examples above was 475 nm, and hence the acquisition of light emission from FIrpic was identified. Each of the host materials for the light-emitting layers used in Examples 22 to 27 and Comparative Examples 7 to 9 is mCP.

TABLE 3

| | Hole-blocking material compound | Luminance ($cd/m^2$) | Voltage (V) | Visual luminous efficiency (lm/W) |
|---|---|---|---|---|
| Example 21 | 1 | 200 | 8.3 | 3.0 |
| Example 22 | 7 | 200 | 8.2 | 3.1 |
| Example 23 | 9 | 180 | 7.5 | 3.0 |
| Example 24 | 26 | 220 | 8.4 | 3.3 |
| Example 25 | 56 | 180 | 6.8 | 3.3 |
| Example 26 | 57 | 190 | 7.0 | 3.4 |
| Example 27 | 94 | 190 | 7.2 | 3.3 |
| Comparative Example 7 | — | 140 | 8.7 | 2.0 |
| Comparative Example 8 | H-1 | 170 | 8.2 | 2.6 |
| Comparative Example 9 | H-2 | 180 | 8.3 | 2.7 |

As can be seen from Table 3, Examples 21 to 27 each using the carborane compound of the present invention in the hole-blocking layer show characteristics more satisfactory than those of Comparative Example 7 using no hole-blocking material and Comparative Examples 8 and 9 using other compounds.

INDUSTRIAL APPLICABILITY

The material for an organic electroluminescent device of the present invention provides an excellent organic electroluminescent device when incorporated into at least one of organic layers of an organic EL device having a structure in which an anode, the organic layers, and a cathode are laminated on a substrate. A light-emitting layer, an electron-transporting layer, or a hole-blocking layer is suitable as the organic layer into which the material is incorporated. Here, when the material is used in the light-emitting layer, the material can be used as a host material for the light-emitting layer containing a fluorescent light-emitting, delayed fluorescent light-emitting, or phosphorescent light-emitting dopant. In addition, the compound of the present invention can be used as an organic light-emitting material that radiates fluorescence and delayed fluorescence.

REFERENCE SIGNS LIST

1 substrate, 2 anode, 3 hole-injecting layer, 4 hole-transporting layer, 5 light-emitting layer, 6 electron-transporting layer, 7 cathode

The invention claimed is:

1. A material for an organic electroluminescent device, comprising a carborane compound represented by the general formula (1):

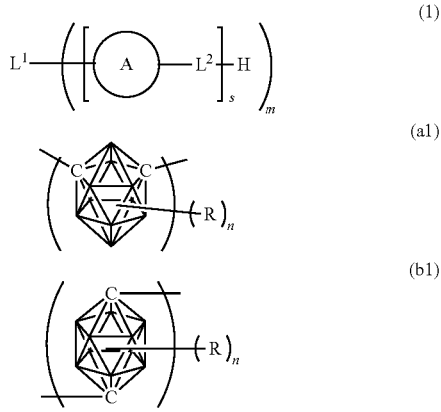

where:
a ring A represents a divalent carborane group represented by the formula (a1) or the formula (b1), and when a plurality of the rings A's are present in a molecule thereof, the plurality of the rings A's may be identical to or different from each other, s represents a number of repetitions and represents an integer of 1 or 2, and m represents a substitution number and represents an integer of 1 to 4, provided that when m=2, s=1;

in formulas (1a) and (1b), (R)$_n$ is bonded to one or more boron atom(s) of the carborane ring;

L$^1$ represents a single bond, an m-valent substituted or unsubstituted aromatic hydrocarbon group having 6 to 30 carbon atoms, an m-valent substituted or unsubstituted aromatic heterocyclic group having 3 to 30 carbon atoms, or an m-valent linked aromatic group formed by linking 2 to 6 aromatic rings of the aromatic hydrocarbon group or the aromatic heterocyclic group, in a case except m=2, L$^1$ is free from representing a single bond, and in a case where m=2, L$^1$ represents a group containing at least one aromatic heterocyclic group or a single bond;

L$^2$'s each independently represent a single bond, or a divalent substituted or unsubstituted aromatic hydrocarbon group having 6 to 30 carbon atoms, a divalent substituted or unsubstituted aromatic heterocyclic group having 3 to 30 carbon atoms, or a divalent linked aromatic group formed by linking 2 to 6 aromatic rings of the aromatic hydrocarbon group or the aromatic heterocyclic group, and L$^2$-H at a terminal may represent an alkyl group having 1 to 12 carbon atoms, an alkoxy group having 1 to 12 carbon atoms, or an acetyl group;

R's each independently represent a substituted or unsubstituted aromatic hydrocarbon group having 6 to 30 carbon atoms, a substituted or unsubstituted aromatic heterocyclic group having 3 to 30 carbon atoms, or a linked aromatic group formed by linking 2 to 6 aromatic rings of the aromatic hydrocarbon group or the aromatic heterocyclic group, and n represents an integer of 1 or 2;

when L$^1$ or L$^2$ represents a substituted aromatic hydrocarbon group, a substituted aromatic heterocyclic group, or a substituted linked aromatic group, each substituent is selected from the group consisting of a diarylamino group having 1 to 30 carbon atoms, an alkyl group having 1 to 12 carbon atoms, an alkoxy group having 1 to 12 carbon atoms, and an acetyl group; and when R represents an aromatic hydrocarbon group, an aromatic heterocyclic group, or a linked aromatic group, the group may have a substituent, and the substituent comprises a diarylamino group having 1 to 30 carbon atoms, an alkyl group having 1 to 12 carbon atoms, an alkoxy group having 1 to 12 carbon atoms, or an acetyl group.

2. A material for an organic electroluminescent device according to claim 1, wherein in the general formula (1), the ring A represents a divalent carborane group represented by the formula (a1).

3. A material for an organic electroluminescent device according to claim 1, wherein the material comprising the carborane compound represented by the general formula (1) is a material comprising a carborane compound represented by the general formula (2):

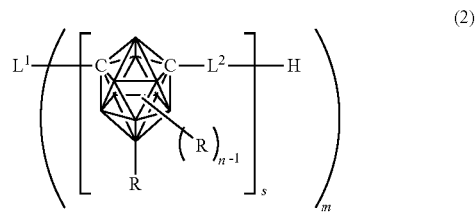

where L$^1$, L$^2$, R, s, m, and n each have the same meaning as that in the general formula (1).

4. A material for an organic electroluminescent device according to claim 3, wherein L$^1$ and L$^2$ each independently represent a substituted or unsubstituted aromatic hydrocarbon group having 6 to 18 carbon atoms, a substituted or unsubstituted aromatic heterocyclic group having 3 to 17 carbon atoms, or a linked aromatic group formed by linking 2 to 6 aromatic rings selected from the aromatic hydrocarbon group and the aromatic heterocyclic group.

5. A material for an organic electroluminescent device according to claim 3, wherein L$^1$ and L$^2$ each independently represent a substituted or unsubstituted aromatic heterocyclic group having 3 to 30 carbon atoms, or a linked aromatic group formed by linking 2 to 6 aromatic rings selected from the aromatic heterocyclic groups.

6. A material for an organic electroluminescent device according to claim 3, wherein m represents an integer of 1.

7. An organic electroluminescent device having a structure in which an anode, an organic layer, and a cathode are laminated on a substrate, the organic layer comprising an organic layer containing the material for an organic electroluminescent device of any one of claims 1 to 3 and 4 to 6.

8. An organic electroluminescent device according to claim 7, wherein the organic layer containing the material for an organic electroluminescent device comprises at least one layer selected from the group consisting of a light-emitting layer, an electron-transporting layer, and a hole-blocking layer.

9. An organic electroluminescent device according to claim 7, wherein the organic layer containing the material for an organic electroluminescent device comprises a light-emitting layer containing a phosphorescent light-emitting dopant.

10. An organic electroluminescent device according to claim 9, wherein an emission wavelength of the phosphorescent light-emitting dopant has an emission maximum wavelength at 550 nm or less.

* * * * *